US008642348B2

(12) United States Patent
O'Fallon et al.

(10) Patent No.: US 8,642,348 B2
(45) Date of Patent: Feb. 4, 2014

(54) DIRECT METHOD AND REAGENT KITS FOR FATTY ACID ESTER SYNTHESIS

(75) Inventors: James V. O'Fallon, Pullman, WA (US);
Charles T. Gaskins, Pullman, WA (US);
Jan R. Busboom, Pullman, WA (US);
Mark L. Nelson, Palouse, WA (US);
Brian J. Kraft, Moscow, ID (US)

(73) Assignee: Washington State University, Pullman, WA (US)

( * ) Notice: Subject to any disclaimer, the term of this patent is extended or adjusted under 35 U.S.C. 154(b) by 63 days.

(21) Appl. No.: 12/522,701

(22) PCT Filed: Jan. 10, 2008

(86) PCT No.: PCT/US2008/050799
§ 371 (c)(1),
(2), (4) Date: Mar. 23, 2010

(87) PCT Pub. No.: WO2008/086495
PCT Pub. Date: Jul. 17, 2008

(65) Prior Publication Data
US 2010/0197029 A1    Aug. 5, 2010

Related U.S. Application Data

(60) Provisional application No. 60/884,385, filed on Jan. 10, 2007, provisional application No. 60/938,860, filed on May 18, 2007.

(51) Int. Cl.
*G01N 33/92* (2006.01)
*C07C 51/00* (2006.01)

(52) U.S. Cl.
USPC ............. 436/71; 436/174; 436/175; 436/177; 554/124

(58) Field of Classification Search
USPC ............. 436/60, 71, 100, 127, 131, 132, 174, 436/175, 177, 178; 422/430; 554/124
See application file for complete search history.

(56) References Cited

U.S. PATENT DOCUMENTS

| | | | | |
|---|---|---|---|---|
| 3,830,789 A * | 8/1974 | Garrett et al. | 530/208 |
| 4,118,407 A * | 10/1978 | Red et al. | 554/178 |
| 5,468,887 A * | 11/1995 | Gupta | 554/169 |
| 5,800,782 A * | 9/1998 | Hagstrom et al. | 422/75 |
| 6,399,800 B1 * | 6/2002 | Haas et al. | 554/156 |
| 6,855,838 B2 * | 2/2005 | Haas et al. | 554/156 |
| 7,777,085 B2 * | 8/2010 | Berry et al. | 568/864 |
| 2007/0048848 A1 * | 3/2007 | Sears | 435/134 |

OTHER PUBLICATIONS

O'Fallon et al. Journal of Animal Science, vol. 85, Feb. 12, 2007, pp. 1511-1521.*

* cited by examiner

*Primary Examiner* — Maureen Wallenhorst
(74) *Attorney, Agent, or Firm* — Barry L. Davison; Davis Wright Tremaine LLP

(57) ABSTRACT

Provided are efficient, cost-effective and water tolerant methods (e.g., single-vial methods) for preparing fatty acid esters from organic matter, including: obtaining organic matter having at least one fat substituent, contacting the organic matter in a reaction mixture with a basic solution under conditions suitable to provide for hydrolytic release of monomeric fatty acids from the at least one fat substituent to provide a base-treated reaction mixture, and esterifying the monomeric fatty acids of the base-treated reaction mixture by acidification of the reaction mixture and treating in the presence of an organic alcohol to provide fatty acid esters. The methods optionally further include, prior to esterifying, neutralizing the base-treated reaction mixture to provide for neutralized fatty acids, separating the neutralized fatty acids from the neutralized reaction mixture, and dissolving the separated fatty acids in the esterification reaction mixture. Also provided are related methods and kits for fat analysis.

27 Claims, 5 Drawing Sheets

DIRECT METHOD AND REAGENT KITS FOR FATTY ACID ESTER SYNTHESIS

CROSS REFERENCE TO RELATED APPLICATIONS

This application claims the benefit of priority to U.S. Provisional Patent Application Ser. Nos. 60/884,385, filed 10 Jan. 2007 and entitled "DIRECT METHOD AND REAGENT KITS FOR FATTY ACID ESTER SYNTHESIS," and 60/938,860, filed 18 May 2007 of same title, both of which are incorporated herein by reference in their entirety.

FIELD OF THE INVENTION

Aspects of the invention relate generally to methods for fatty acid analysis of biological materials, and methods for digestion and conversion of biomass to produce fatty acid esters and various other biological materials and products (e.g., biodiesel).

BACKGROUND

Herein, methods for the synthesis of fatty acid esters (FAE) are described. Such methods are important in the analysis of fatty acids from foodstuffs and in the production of diesel fuel from biological sources (e.g., biodiesel or fatty acid methyl ester). While differing elements are of relevance to the disparate fields, both areas would benefit from a simple, robust method for the synthesis of FAE from biological materials.

The analysis of fatty acids has become increasingly important due largely to nutritional and health implications. Therefore, a method for analyzing fatty acids that provides rapid results without modification of the constituent fat compositions is of great value. Many methods are currently used to analyze fatty acids (e.g., Morrison and Smith, 1964; Sukhija and Palmquist, 1988; Kazala et al., 1999; Mir et al., 2002; Nuemberg et al., 2002; Budge and Iverson, 2003; Cooper et al., 2004). These methods, generally, are not convenient or direct, and often must be optimized for reaction conditions, including the catalyst and the temperature (Lewis et al., 2000; Park et al. 2002; Shahin et al., 2003). Ideal methods, as noted by Palmquist and Jenkins (2003) would determine the total fatty acid concentration in tissues, oils, and feed samples by converting fatty acid salts, as well as the acyl components in all lipid classes such as triacylglycerols, phospholipids, sphingolipids, and waxes, to FAE using a simple direct esterification procedure.

Current methods for FAE synthesis utilized for fat analysis require extensive sample pre treatment to eliminate the presence of water. Many of the common reagents employed within the esterification process are water sensitive (e.g. $BF_3$, $NaOCH_3$, $NaOCH_2CH_3$). Moreover, because the esterification reaction is an equilibrium wherein water is formed as a product, lower concentrations of water favor product formation. As a result, even within methods known to the art employing non water-sensitive reagents (e.g., $H_2SO_4$, HCl, NaOH), efforts to eliminate water from the reaction mixture are extensive and time consuming. These attributes of current methodologies underlie the pervasive recognition in the art that water within the reaction mixture decreases yield and reaction rates in FAE synthesis—thus water must be avoided in FAE synthesis. Within such methods, once the sample has been dried, incomplete dissolution &/or reconstitution of the sample within the water-free media also leads to decreased yields of FAE's due to the kinetic restrictions imposed on the system. Current methodologies employ extended reaction times to overcome such limitations, however as noted in the art extended reaction times also lead to increased degradation of polyunsaturated fats which alters the determination of a samples fat composition.

Likewise, the production of diesel fuel from biological sources is of growing interest. Generally, methodology employed in the synthesis of fatty acid esters (FAE) for biodiesel is similar to that employed within the analysis of fatty acids. A primary difference however is the focus on market-driven cost pressure, and the process cost is prominent in the practical production of biodiesel. The largest single cost of biodiesel production is the cost of the feedstock. Extensive extraction and processing of any oil-rich biomass is typically required and often employs extensive oil extraction (via oilseed crushing or solvent extraction with hexane or similar) and drying prior to the introduction of the oil into the fatty acid ester synthesis process. In addition to the concerns relating to the presence of water, yield of FAE and ensuring the final FAE product does not contain free fatty acid anion (FFAA) are of particular concern in the production of biodiesel. FFAA causes fuel combustion and corrosion problems and therefore is undesirable in fuel mixtures.

Considerations deriving from the costs and hazards of methods for oil extraction have led to a large body of work directed at minimization of FFAA concentrations and extraction process simplification. The former has focused primarily on FFAA in feedstocks (Hass et al., U.S. Pat. No. 6,399,800) and FFAA reprocessing (Stern et al. U.S. Pat. No. 5,424,466), while methods for FAE synthesis from low value, high FFAA concentrations feedstocks have been developed (Hass, et al. U.S. Pat. No. 6,855,838) in attempts to minimize feedstock costs. Additional methods for simplifying the extraction process (Hass et al. U.S. Pat. No. 7,612,221) for use in feedstocks with lipid-linked fatty acids have been developed.

Common to both fatty acid analysis and biofuel production, there is a pronounced need in the art for simple, rapid & robust methods for the dissolution and esterification of samples or feedstocks containing complex mixtures and/or heterogeneous structures.

SUMMARY

Provided are efficient, cost-effective and water tolerant methods (e.g., single-vial methods) for preparing fatty acid esters from organic matter, comprising: obtaining organic matter comprising at least one fat substituent, contacting the organic matter in a reaction mixture with a basic solution under conditions suitable to provide for hydrolytic release of monomeric fatty acids from the at least one fat substituent to provide a base-treated reaction mixture, and esterifying the monomeric fatty acids of the base-treated reaction mixture by acidification of the reaction mixture and treating in the presence of an organic alcohol to provide fatty acid esters. The methods optionally further comprise, prior to esterifying, neutralizing the base-treated reaction mixture to provide for neutralized fatty acids, separating the neutralized fatty acids from the neutralized reaction mixture, and dissolving the separated fatty acids in the esterification reaction mixture. Also provided are related methods and kits for fat analysis.

Particular aspects provide a simplified protocol to obtain fatty acid esters (FAE) directly from plant or animal tissue, microbes, oils, or oil rich feedstocks is disclosed herein. With this protocol, FAE synthesis is conducted in the presence of high concentrations of water (e.g., including concentrations at or above 35% v/v, and which may derive at least in-part from the feedstock), and does not require oil extraction or feedstock pre-processing. Wet tissues, or other feedstocks are optionally ground or pretreated in a manner to increase the surface to volume ratio of the material, and then subjected to permeabilization and base hydrolysis in the presence of an organic alcohol and water; that is, pretreated material is permeabilized and/or hydrolyzed in a basic (e.g. contains a Lewis Base) organic alcohol (e.g Methanol, Ethanol, Glycerol, Propanol) solution (e.g., mixture) containing water. The resulting solution is neutralized and/or acidified and the free fatty acid anions are esterified by acid catalysis. The process steps will be suitably specific to the purpose for FAE use (analysis or biodiesel production) and may involve any number of intervening solid/liquid and/or liquid/liquid extraction methodologies. For applications in fat analysis, an organic extracting solvent is then added to the reaction mixture, which is vortex-mixed and centrifuged. The resultant layer of the organic extracting solvent is transferred into a GC vial for subsequent gas chromatography. All reactions may be conducted in a single tube for convenience. The method meets a number of criteria for fatty acid analysis including not isomerizing conjugated linoleic acid (CLA) or introducing fatty acid artifacts. For applications in biofuels a phase separation optionally through centrifugation or solvent extraction may be employed to yield substantially pure FAE. Depending on the feedstock any variety of intervening separation methods to remove byproducts dot desirable for biodiesel production may be introduced at any point in the process.

The methods described herein are applicable to any feedstock, examples include but are not limited to; fresh, frozen, or lyophilized tissue samples, animal fats, animal or veritable oils, greases, waxes, algae and agricultural and/or biological products hereinafter collectively referred to as organic matter. Preferably the method is designed to be applied to organic matter with a high fat content, wherein the term 'fat' is intended to encompass all forms of fats; saturated and unsaturated fatty acids, lipids, mono-, di- and triglycerides and the like. Methods applied to algae, or to other water-rich biomass are particularly preferred, as the high, natural water content of such biomass has profoundly discouraged its use as a source of fatty acid esters (FAE) in the context of prior art methods. Optimally, the method would be utilized with feedstocks wherein little or no preprocessing to refine and/or alter the component fat composition of the feedstock was employed prior to FAE synthesis. The method saves time, effort and is economical when compared to other methods. Its unique performance, including non-costly sample preparation, is achieved because the FAE reaction mixtures are not significantly sensitive to the presence of water, and thus may be carried out without the need for stringent atmospheric controls offering a particular cost advantage for the production of biodiesel from water or free fatty acid FFA, or FFAA-rich feedstocks.

DETAILED DESCRIPTION

A method for the synthesis of fatty acid esters (FAE) from nominally processed or raw, unprocessed organic matter (e.g. a feedstock or sample) is described herein. Implementations wherein the method is directed to the analytical characterization of a sample may be carried out in a single container utilizing common chemical reagents and lends itself to the potential for distribution of simple kits or automated systems containing the necessary reagents and/or containers necessary for the FAE synthesis. The method comprises an optional pretreatment of the matter to increase the surface area to volume ratio, digesting the material in a mixture containing a base (e.g. contains a Lewis Base), and optionally an organic alcohol and optionally water to yield principally FFAA and other hydrolyzed organic matter, an optional separation of non-suspended solids and/or other mixture constituents and subsequent esterification of the FFAA by acidifying the solution then, depending on the indented use of the FAE, extraction of the FAE utilizing one or more of the following methods; 1) extraction with an organic solvent that is not miscible with the reagent mixture, 2) centrifugation or 3) phase separation through settling, and optional subsequent FEA refinement. Depending on the intended use of the FAE and composition of the feedstock, any number of intervening separation methods may be employed to separate components of the mixture during the process. The ability to alter process and introduce intervening steps for the accommodation of a variety of feedstocks is a primary advantage of the method.

Figure 4:
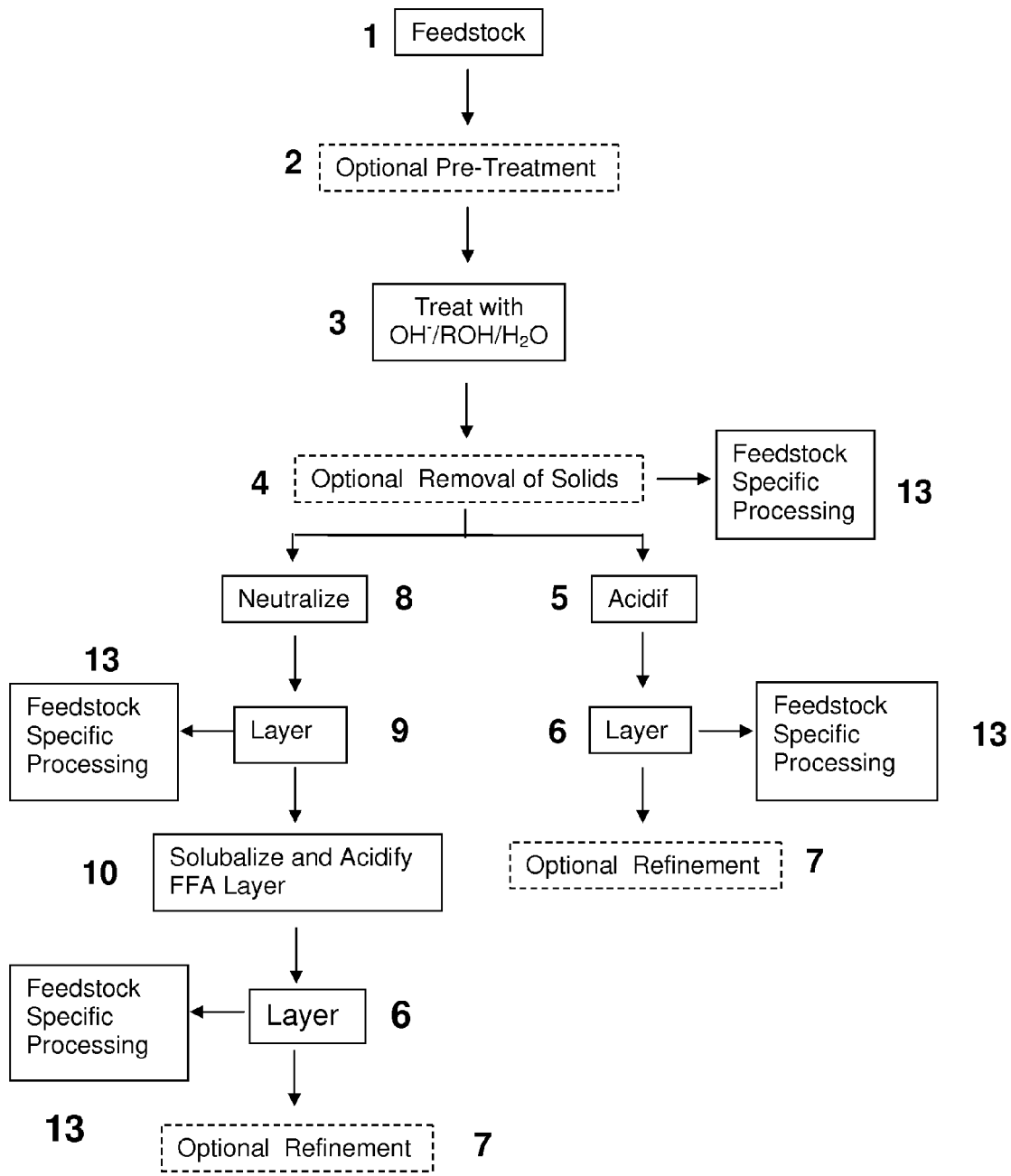
FIG. 4 shows a flow chart of exemplary embodiments of methods for preparing fatty acid esters from organic matter according to aspects of the present invention.

FAE production. Exemplary FAE production method aspects of the invention can be understood with reference to the flow-chart of FIG. 4. According to FIG. 4, a Feedstock 1 is treated 3 with a base (e.g., Lewis base) in the presence of an organic alcohol (e.g., methanol, ethanol, glycerol, propanol, etc.) and water (e.g., at least 1% v/v water). An optional Pre-treatment step 2 (e.g., chopped or ground prior to digestion and hydrolysis) may be included prior to base treatment 3.

In particular embodiments it may be desirable to introduce an optional Pre-treatment step, 2, to increase the efficiency of the process. Such pretreatment may utilize methods including but not limited to grinding, chopping, sonicating, mashing or pulverization of the sample to increase the surface area to volume ratio of the sample to provide an increased kinetic access for hydrolysis. This step is optional and is not required for utilization of the method. In some cases it will however decrease both the amount of time necessary to fully digest the sample and the overall efficiency of the digestion process.

Digestion of the organic matter in step 3 is carried out in a mixture containing base, and optionally water, and an optional organic alcohol. Herein a base is considered as any substance that can be considered as a 'Lewis base'. Lewis bases, which are known to those in the art, as chemicals or ions that have the ability to donate an electron pair to a Lewis acid. Preferably the base comprises a mineral base (e.g., $X(OH)_n$ wherein X=Na, K, Mg, or other metal and n=1-10). For the purposes of digestion, the alcohol (e.g., 20% v/v or greater) and water (including up to 35% v/v or greater) are optionally present in a solution suitable to largely solubilize the sample. Preferably the solvent comprises an organic alcohol, however most any solvent may be employed in this step. The importance of the sample digestion is twofold: 1) Decompose the organic matter into small soluble colloids and/or molecules and 2) Principally convert complex fats (e.g., triglycerides) into monomeric FFAA. The presence of the base in molar excess and water assists in both goals, and ideally the organic solvent would also serve to assist in both. Most any organic solvent and mixtures thereof are contemplated here, provided the solvent assists in the dissolution of the organic matter. When contemplating the large scale deployment of the process, cost considerations and waste utilization will largely influence the choice of organic solvent, base.

The digestion step, 3, is preferably carried out at temperatures between 0-100° C. for a period of 10 sec to 100 hr, depending primarily on section scale, optimally the resultant solution would be mixed (e.g. stirred, shaken, agitated via bubbling) throughout the digestion process and carried out for between about 0.5 and 100 hours, however the specific timing will be largely dependent on the scale (size) of the batch and the nature and physical condition of the organic matter.

Subsequent to the digestion step, 3, an optional separation step 4, may be introduced. Generally, the function of a separation step 4 is to remove non-fat containing matter from the reaction mixture for feedstock specific processing, 13. The separation step 4, may involve any one of the physical separation methods known to the art. Particular embodiments may involve the removal of non-suspended or settled solids from the mixture, via a liquid/solid separation mechanism (e.g. filtration). Depending on the temperature, pH, and fat composition of the mixture specific treatments to solidify and selectively remove the FFAA in the form of precipitated soap.

In particular embodiments (e.g., right arm of process divergence of FIG. 4), subsequent to base treatment 3, the reaction mixture is acidified in process step 5, through the controlled addition of acid (e.g. HCl, $H_2SO_4$, HBr, $HNO_3$, $H_3PO_4$, $H_2CO_3$, $CH_3CO_2H$) until the resting concentration of acid is about 0.5-10 molar. The final concentration of acid in process step 5 will be dependent on the necessary catalytic rate for esterification, feedstock composition and reaction volume. Large scale implementations may require acidification via the introduction of acidified steam and thus may be difficult to specifically quantify. A critical aspect of the acidification step, 5, is the presence of organic alcohol in a significant concentration (e.g. equal to or greater than: about 5%, about 10%; about 15%; about 20%; about 25%; or about 30%). Preferably, organic alcohol is present in an amount of at least about 20%. In the preferred embodiment the organic alcohol is methanol, which under acidic conditions will reach with FFAA to yield a fatty acid methyl ester (e.g. FAME or biodiesel), however it is to be understood, any organic alcohol may work for the process. In particular embodiments, an alcohol mixture may be present.

The acidification step, 5, is preferably carried out at temperatures between 0-100° C. for a period of 10 sec to 100 hr, depending primarily on section scale, optimally the resultant solution would be mixed (e.g. stirred, shaken, agitated via bubbling) throughout the digestion process and carried out for between about 0.5 and 100 hours, however the specific timing will be largely dependent on the scale (size) of the batch and the nature and physical condition of the organic matter.

Once the FAE is present, if the solvent mixture in acidification step 5 is sufficiently polar (hydrophilic), an, at least, two phase layered system will spontaneously result wherein a floating, or top, solvent layer containing principally FAE forms. In particular embodiments, the acidified mixture from step 5, may be transferred to a settling tank, or similar container, wherein the layering step, 6 can commence. If the acidified mixture is not sufficiently polar, water may be added to the mixture subsequent to the acidification step to initiate the layering step, 6.

Upon layering, 6 the FAE is separated from the other mixture constituents, which can be fed into additional feedstock specific processing, 13. In particular embodiments, the separated FAE, may undergo additional processing, 7, to dry, fractionalize, chemically treat or otherwise refine the FAE product. Such processing will again be feedstock specific and depend on the desired end use of the FEA products.

In particular embodiments (e.g., left arm of process divergence in FIG. 5), subsequent to base treatment 3, the reaction mixture is neutralized in process step, 8, via the controlled addition of acid in a manner similar to process step 5, with the primary difference that the addition of acid stops once the mixture has reached a near neutral (e.g. pH 5-9) state. The neutralization step, 8, provides means for controlled fractionalization of FFAA constituents. Neutralization will convert the FFAA to the neutral free fatty acid (FFA), which will be significantly non-miscible within solutions of high polarity. Utilizing temperature (e.g. heating or cooling) and mixture polarity (e.g. addition of water, or other solvents) FFA precipitation can be initiated to yield a solid FFA layer during the neutralization step 8. The invention contemplates the use of controlled FFA layering to isolate specific FFA constituents, accordingly neutralization step 8 may comprise multiple FFA precipitation and separation steps.

Once the FFA layer is formed, the FFA can be separated from the layered system. The other non-fat constituents may then be fed into other, feedstock specific processing, 13, and the solidified FFA layer is dissolved in an acidic alcoholic medium in process step 10. Similar to process step, 5, the principle function of step 10 is to convert the fat components to FAE. The primary functional difference between process steps 5 and 10, is the necessity to soluablize the FFA. Accordingly, process step 10 may comprise a sequential dissolution of FFA in mixture principally composed of an organic alcohol with subsequent addition of an aqueous acid to the resultant mixture. In certain embodiments the addition solid FFA may be dissolved directly into an acid/alcohol/water mixture. Similar to acidification step 5, the resultant mixture containing the FFA contains organic alcohol in an amount equal to or greater than: about 5%, about 10%; about 15%; about 20%; about 25%; or about 30%). Preferably, organic alcohol is present in an amount of at least about 20%. In preferred embodiments the organic alcohol is methanol, which under acidic conditions will reach with FFAA to yield a fatty acid methyl ester (e.g. FAME or biodiesel), however it is to be understood that any organic alcohol may work for the process. In particular embodiments, an alcohol mixture may be present.

The acidification step, 10, is preferably carried out at temperatures between 0-100° C. for a period of 10 sec to 100 hr, depending primarily on section scale, optimally the resultant solution would be mixed (e.g. stirred, shaken, agitated via bubbling) throughout the digestion process and carried out for between about 0.5 and 100 hours, however the specific timing will be largely dependent on the scale (size) of the batch and the nature and physical condition of the organic matter. Once the FAE is formed in step 10 subsequent layering 6 and optional refinement 7 yield FAE with desired characteristics.

Fatty Acid Analysis Methods.

Figure 5:
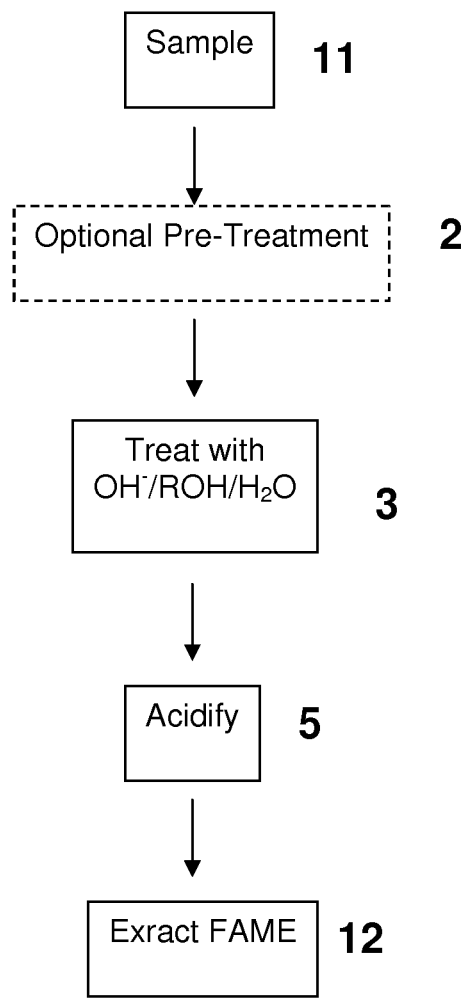
FIG. 5 shows a flow chart of exemplary embodiments of methods for fat analysis of organic matter according to aspects of the present invention.

Exemplary fat analysis aspects of the invention can be understood with reference to the flow-chart of FIG. 5. According to FIG. 5, a sample 11, which may or may not be fat rich, is treated 3 with a base (e.g., Lewis base), and optionally in the presence of an organic alcohol (e.g., methanol, ethanol, glycerol, propanol, etc.) and water (e.g., at least 1% v/v water). An optional Pre-treatment step 2 (e.g., chopped or ground prior to digestion and hydrolysis) may be included prior to base treatment 3. Subsequent to base treatment 3, the reaction mixture is acidified 5. After acidification a solvent extraction step, 12, provides means for the selective extraction of the FAE constituents for subsequent analysis. In extraction step 12a significantly hydrophobic solvent (e.g. hexane, benzene, methylene chloride, chloroform, etc) is added to the reaction mixture from step 5. The addition of the hydrophobic results in a solvent layer containing the FAE constituents, that can subsequently be withdrawn from the mixture (e.g via a syringe, or similar device) for analysis (e.g GC, MS).

The steps of sample digestion, esterification and extraction as described by the method for fat analysis may be carried out within a single vessel. While secondary container may be required to house reagents and/or selectively remove hydrophobic or hydrophilic layer(s) the method allows for an efficient use of materials and other consumables. While the use of a single vessel is not required by the method it provides an optimal process with little waste or loss associated with transferring the reaction mixture. Moreover the method is simplified such that it becomes adaptable to simple kits and/or automated methodology.

Many methods for quantization of fatty acids require the presence of a standard fatty acids and/or fatty acid esters. Accordingly, a standard or mixture of standards may be added to the reaction mixture at any point throughout the process. The timing of the addition will dictate the nature of the standards added. Specifically if the standards are added after the esterification step fatty acid esters will be utilized as standards, while fatty acids or fatty acid esters can be added prior to esterification. The timing of addition, quantity and specific identity of the standards used in the method will depend on the goals for the addition, and will be apparent to one skilled in the art. The addition of standards is optional and will depend on the interests and goals of the artisan. As a matter of convenience, a kit or automated system for execution of this analysis could be marketed and provided to end user organizations. The kit would contain reagents and instructions necessary for material digestion. A kit or automated system would comprise treatment with the following elements: 1) a basic (e.g. contains a Lewis Base) organic alcohol solution (which may or may not contain water); 2) an acidic (e.g., contains a Lewis Acid) solution wherein the solvent may be a polar organic solvent, water or some mixture thereof and optionally; 3) a hydrophobic solvent capable of solubilizing esterified fatty acids that is not miscible with solution resulting from mixing the component solutions 1 and 2. Additional components may include instructions and/or instruments to optional sample pretreatment, digestion, processing and/or analysis or the resulting products. Reagent vials for digestion and esterification may also be included in said kits.

An automated system, wherein the steps of the FAE synthesis described herein are carried out in sequence are anticipated as a simple extension of the invention. All the steps require simple additions of material to a single reaction vessel or transfer of the reaction mixture to subsequent vessels. Once transferred or added to the appropriate vessel, simple heating & mixing (e.g. shaking, stirring) may be required during the incubation steps. Instrumentation performing all such tasks is widely available and would require only minor modifications to accommodate the method described herein. Such automation, instrumentation and kits are all applicable to implementations in the analytical analysis of fatty acids and the industrial production of biodiesel.

The exemplary embodiments for fat analysis use familiar and economical chemicals, methanol, potassium hydroxide, sulfuric acid, and hexanes however given the mechanism of action one could envision the use of any acid/base/organic solvent(s) combination wherein the sample of interest is first digested to release monomeric fatty acids from triglycerides and other complex molecules with a base. Particular interest, may derive from the judicious choice of acid and base; upon neutralization/acidification a salt will be formed and the process economics may favor a particular base/acid combination. For example, the use of KOH in combination with $H_3PO_4$, yields a potassium phosphate salt, a salt with a defined market, as a "waste" product. The digestion step, 3 is aided by the presence of water, alcohol and base which facilitates the near complete dissolution of the organic matter. Given the structural and chemical heterogeneity provided by potential feedstock compositions, dissolution of the organic matter is a key component that provides for the kinetic availability of the fat containing residues within the organic matter for hydrolytic release of the monomeric FFAA for subsequent acid catalyzed esterification.

In certain embodiments, a feedstock may be naturally water rich (e.g. Algae) and thus may not require addition of water, rather a simple addition of organic alcohol and base to the feedstock can enable dissolution. Methods applied to algae, or to other water-rich biomass are particularly preferred, as the high, natural water content of such biomass has profoundly discouraged its use as a source of fatty acid esters (FAE) in the context of prior art methods.

All of the methods for FAE synthesis currently known to the art require extensive methodology to eliminate the presence of water both in sample pretreatment and throughout the esterification process. This is particularly problematic when one considers the use of water rich feedstock for large-scale processes. For example, Algae represent a particularly promising feedstock for the production of biodiesel, as ~50% of their biomass is comprised of fats, however this benefit is largely offset by the problems associated with the water rich environment Algae is harvested from. The method described herein requires no water removal, and in some cases actively adds water to the reagent mixture and thus provides an optimal method for the production of biodiesel from water rich feedstocks. The presence of water, particularly in the sample digestion step aids in the solubilization of the sample thereby enabling a more efficient, or through, esterification of the fatty acids contained therein. Controlled addition of water to the digestion mixture and/or uncontrolled addition of water are contemplated. The term 'uncontrolled addition' herein refers to the passive acknowledgement of the presence of water in the system (e.g. utilizing 'wet' solvents, caring the reaction out within an open system in a humid atmosphere, not taking stems to ensure the absence of water). Water may be present in all steps of the method as long as the overall concentration of water remains below about 80% v/v during the esterification step. A controlled consideration of the water content may comprise the accounting of the water present in the feedstock in determining the necessity to add water to the digestion mixture.

Optional steps wherein a liquid layer, containing a free fatty acid anion sample is physically separated from non-dissolved organic matter, salts, or other solids may be introduced at any point prior to the esterification step. Such separations are generally not applicable when operating at analytical scales. The separation may be carried out employing any one of the multitude of liquid/solid or liquid/liquid separation methods known to the art. Generally such separations will serve to the end of extracting other valuable, reusable, or interfering, non-fat based feedstock constituents. Process modifications to enable such separations are contemplated. In certain embodiments, the basic, digestion mixture may the neutralized, generating an insoluble fat layer, comprised principally of neutral free fatty acid anion this layer can be physically separated, subsequently dissolved in an acidic alcohol solution- to convert to FAE.

Base catalyzed transesterification of mono-, di- and triglycerides have long been known to the art. Generally, attempts to minimize the water content of such reaction mixtures are considered preferable as the hydroxide ion in water acts as a competing nucleophile in the transesterification reaction. Herein it is demonstrated that, water sensitivity can be avoided by first converting the feedstock to free fatty acid anion then using acid catalyzed esterification-surprisingly the presence of water has a nominal effect on the esterification of fatty acids when present in concentrations below 80% v/v. As a result, efforts to minimize the water content of fatty acid esterification reaction mixtures are not required to obtain results comparable to methodology commonly employed in the art. Critically, the method described herein greatly alters the economics of biodiesel production—by providing a method for FAE production that does not mandate the use of refined, or water free, feedstocks. Retirement Once esterification of the sample has been completed, extraction of the fatty acid esters may be preformed via solvent extraction, centrifugation and/or spontaneous formation of a FAE layer.

Common to extraction methods, a second, hydrophobic solvent is added to the hydrophilic reaction mixture. Because the hydrophobic and hydrophilic solvents are ideally non-miscible two solvent layers form. Through repeated mixing of the two solvent system, the fatty acid esters are extracted from the hydrophilic reaction mixture into the hydrophobic layer of the two solvent system. In some embodiments, formation of the two layered system may not be spontaneous, rather the sample may require centrifugation or addition of more hydrophilic solvent(s) (e.g. water) or other methods common to solvent extraction. Irrespective of how the layers are formed, the fatty acid esters are present predominantly in the hydrophobic layer, which can then be selectively removed and subsequently analyzed. In some embodiments multiple extractions may be preformed on the same reaction mixture. The resulting hydrophobic layers may be combined and subsequently subjected to analysis or independently subjected to analysis. Optionally, methods to reduce the volume of the hydrophobic layers of FAE may be employed to increase the concentration of the FAE within the hydrophobic layer.

The method described herein is based upon a surprising conception comprising the use of high concentrations of base, inclusion of the presence of water in the digestion of organic matter and the tolerance to significant concentrations of water in the fatty acid ester (FAE) synthesis process, which comprises organic alcohol, as described herein. Previous methods in the art for FAE synthesis have rigorously avoided water as a matter of standard procedure—this adds both cost and time to the overall process. Although the method described herein requires two steps, it may be carried out within a single reaction vessel. The introduction of various solid/liquid or liquid/liquid separations to enable the extraction of mixture constituents of interest, value or those which interfere in the FEA synthesis is contemplated here, and will be specific to the feedstock and scale of the process.

The method described herein allows for the presence of water in FAE synthesis, therefore eliminating the drudgery of special sample preparation, e.g., freeze-drying, or extensive seed processing and oil refinement are no longer necessary. Preferably organic matter can be analyzed/processed in the state it is obtained—for large scale implementations, wherein process costs are of primary concern, the method described herein offers a particular advantage via a decreased cost/expense for feedstock pre-processing (drying). Thus, for examples, meat and milk samples can be analyzed directly without any prior dehydration step and raw, unprocessed biodiesel feedstocks can be directly treated to yield FAE. Optional pretreatment steps to grind, or chop the sample may be desirable to decrease the digestion time, however the use of such methods will largely be dictated by the size and physical state of the sample prior to analysis and are not mandated by the method. Allowing for the presence of water in the reagent mixture allows for enhanced organic matter dissolution thereby facilitating the total extraction of fatty acids from said sample, such extraction has not been realized in the art. Importantly, water does not interfere with the esterification of any fatty acid, and can be present throughout the process.

In summary, a simplified protocol developed to obtain fatty acid esters (FAE) from any sample is described herein. The method consists of two steps, optionally conducted in a single reaction tube. The protocol relies on the presence of water, which heretofore, had been rigorously and tediously eliminated from the sample prior to utilization of FAE synthesis methods known to the art. Since water is part of the method described herein, and not antagonistic to it, sample preparation is rapid; one only weighs-out or pipettes the sample into a vessel and then conducts the direct FAE synthesis. The preparation time it takes to lyophilize a sample (usually days), or the prior organic solvent extractions and nitrogen evaporations (usually hours) that are required to eliminate water in the fatty acid methods known to the art are no longer required. The removal of this requirement both drops the cost of the process by relieving the stringent feedstock pre-processing steps, and introduces the possibility of utilization of both water an fat rich feedstocks (e.g. algae).

To assess certain features of the method disclosed herein, it was compared to direct FAE synthesis with two processes routinely used for FAE synthesis, namely, the base catalyst sodium methoxide and the acid catalyst boron trifluoride. Samples used with sodium methoxide and boron trifluoride did not contain water, as this would compromise the performance of these two methylating agents.

The examples provided herein were chosen for distinct reasons. The Supelco™ fatty acid standard mixture was chosen because it contained short and long chain saturated, monounsaturated, and polyunsaturated fatty acids in defined amounts and thus served as a primary test of the feasibility of our method. Fish oil was chosen because it is an important source of the long chain polyunsaturated omega-3 esterified eicosapentaenoic (EPA), docosapentaenoic (DPA), and docosahexaenoic (DHA) fatty acids. Conjugated linoleic acid (CLA), as the free acid, was chosen because it is of medical importance as perhaps the only fatty acid that can directly inhibit cancer (Belury, 2002) and because current FAE synthesis methods often cause undesirable isomerizations of this fatty acid (Kramer et al., 1997). Beef longissimus muscle was chosen because of our special interest in beef fatty acids and it serves as a direct test of the ability of direct FAE synthesis to extract and methylate all of the fatty acids present in a meat tissue. To address the problem of refractory samples, we included wax esters, cholesteryl lipid derivatives and alkyl methane sulfonates, as these are difficult fatty acid derivatives to analyze (Palmquist and Jenkins, 2003). Finally, as a concluding demonstration of the versatility of the direct FAE synthesis method, we included a variety of oils, feedstuffs and foods.

Generally a variety of feedstocks were chosen to demonstrate the flexibility of the process. It is to be understood that to utilize ant given feedstock in a process at an industrial scale, e.g. the production of biodiesel, additional separations of non-fat sample constituents may be required to enable economic viability. Any such separations will be feedstock specific and tailored to added value, waste, or interfering constituents. The method described herein enables process and feedstock flexibility, most importantly enabling the use of cheaply available feedstocks with little or no pre-processing.

Exemplary Preferred Embodiments

Particular aspects provide a method for preparing fatty acid esters from organic matter, comprising: obtaining organic matter comprising at least one fat substituent; contacting the organic matter in a reaction mixture with a basic solution under conditions suitable to provide for hydrolytic release of monomeric fatty acids from the at least one fat substituent to provide a base-treated reaction mixture; and esterifying the monomeric fatty acids of the base-treated reaction mixture by acidification of the reaction mixture and treating in the presence of an organic alcohol in an amount equal to or greater than: about 5%, 10%; 15%; 20%; 25%; or 30% v/v, to provide for an esterification reaction mixture, wherein fatty acid esters are provided. In certain embodiments, contacting with the basic solution comprises contacting in the presence of at least one of water, and an organic alcohol. In certain aspects, the organic alcohol is present in the esterification reaction mixture in an amount equal to or greater than about 20% v/v. In particular aspects, water is present in the esterification reaction mixture in an amount equal to or greater than about: 1%; 2%; 3%; 4%; 5%; 10%; 15%; 20%; 25%; 30%; 35%; or 40% v/v. In certain implementations, at least 1% v/v water is present during the contacting with the basic solution, and water is present in an amount less than or equal to 35% v/v during esterification. In certain embodiments, during at least one of contacting with the basic solution and esterifying by treating with acid, water is present in an amount from: about 1% to about 40% v/v; 1% to 35% v/v; 1% to 33% v/v; 1% to 30% v/v; 5% to 40% v/v; 10% 40% v/v; 15% to 40% v/v; 20% to 40% v/v; 25% to 40% v/v; 30% to 40% v/v; 35% to 40% v/v; 10% to 30% v/v; 15% to 25% v/v; 15% to 30% v/v; 20% to 30% v/v; 25% to 30% v/v; or 20% to 35% v/v. In particular aspects, the base comprises a Lewis base or a mineral base, and where the acid comprises an inorganic or an organic acid. In certain embodiments, the mineral base comprises $X(OH)_n$, wherein X comprises Na, K, Mg, or another metal and n is a value from 1-10, and the acid comprises at least one selected from the group consisting of: $H_2SO_4$, HCl, HBr, $HNO_3$, $H_3PO_4$, $H_2CO_3$. In certain implementations, the method further comprises, prior to or during contacting with base, pretreating or treating the organic matter to increase its surface area to volume ratio. In particular aspects, prior to esterifying, undigested solid organic matter, or non-fat containing matter, is removed or otherwise sequestered or separated from the base-treated reaction mixture. In certain embodiments, separation of the undigested solid organic matter from the base-treated reaction mixture comprises at least one of centrifugation, settling, filtering, extraction and phase separation. In certain implementations, subsequent to esterifying, fatty acid esters are separated from other components of the reaction mixture by means of at least one of centrifugation, settling, extraction, liquid/solid separation methods, filtration, and phase separation. In certain aspects, the separation comprises at least one of heating the reaction mixture, cooling the reaction mixture, and altering the polarity of the reaction mixture by addition of water, solvents or other polarity altering agents.

In certain aspects, the method further comprises, prior to esterifying: neutralizing the base-treated reaction mixture to provide for neutralized fatty acids; removing, sequestering or otherwise separating the neutralized fatty acids from the neutralized reaction mixture; and dissolving the separated fatty acids in the esterification reaction mixture. In particular embodiments, subsequent to esterifying, fatty acid esters are separated from other components of the reaction mixture. In certain aspects, separation of fatty acid esters comprises at least one of centrifugation, settling, extraction, liquid/solid separation methods, filtration, and phase separation. In certain implementations, the separation comprises at least one of heating the reaction mixture, cooling the reaction mixture, and altering the polarity of the reaction mixture by addition of water, solvents or other polarity altering agents. In preferred embodiments, the organic matter comprises algae.

Additional aspects provide a method for preparing fatty acid esters from organic matter, comprising: obtaining organic matter comprising at least one fat substituent; treating the organic matter to increase its surface area to volume ratio; contacting the organic matter in a reaction mixture with a basic solution under conditions suitable to provide for hydrolytic release of monomeric fatty acids from the at least one fat substituent to provide a base-treated reaction mixture; removing, or otherwise sequestering or separating undigested solid organic matter or non-fat containing matter from the base-treated reaction mixture; and esterifying the monomeric fatty acids of the base-treated reaction mixture by acidification of the reaction mixture and treating in the presence of an organic alcohol in an amount equal to or greater than: about 5%, 10%; 15%; 20%; 25%; or 30% v/v, to provide for an esterification reaction mixture, wherein esterified fatty acids are provided. In certain implementations, subsequent to esterifying, fatty acid esters are separated from other components of the reaction mixture. In particular aspects, separation of fatty acid esters comprises at least one of centrifugation, settling, extraction, liquid/solid separation methods, filtration, and phase separation. In some aspects, the separation comprises at least one of heating the reaction mixture, cooling the reaction mixture, and altering the polarity of the reaction mixture by addition of water, solvents or other polarity altering agents. In certain embodiments, contacting and esterification are performed within a single vessel. Preferably, the organic matter comprises algae.

Yet further aspects provide a method for fat analysis of organic matter, comprising: obtaining a sample of organic matter comprising at least one fat substituent; contacting the organic matter in a reaction mixture with a basic solution under conditions suitable to provide for hydrolytic release of monomeric fatty acids from the at least one fat substituent to provide a base-treated reaction mixture; esterifying the monomeric fatty acids of the base-treated reaction mixture by acidification of the reaction mixture and treating in the presence of an organic alcohol in an amount equal to or greater than: about 5%, 10%; 15%; 20%; 25%; or 30% v/v, to provide for an esterification reaction mixture, wherein fatty acid esters are provided; and performing qualitative or quantitative analysis on the fatty acid esters. In certain implementations, the method further comprises, prior to or during contacting with base, pre-treating or treating the organic matter to increase its surface area to volume ratio. In certain embodiments, prior to performing analysis, fatty acid esters are separated from other components of the esterification reaction mixture, and separation of fatty acid esters comprises at least one of centrifugation, settling, extraction, liquid/solid separation methods, filtration, and phase separation. In certain aspects, contacting the organic matter with a basic solution and esterification are performed within a single vessel.

Additional aspects provide a kit for fat analysis of organic matter, comprising in one or more vials or reaction vials: a base suitable to facilitate hydrolytic release of monomeric fatty acids from a fat substituent; and an acid suitable, in the presence of an organic alcohol, to facilitate esterification of monomeric fatty acids to provide fatty acid esters. Certain kit embodiments further comprise a hydrophobic solvent suitable to solubilize fatty acid esters. Preferably, the kit further comprises an organic alcohol solvent suitable to solubilize organic matter and participate in the esterification.

Example 1

Methods and Materials

The examples provided herein utilize reagents to produce fatty acid methyl esters (FAME), and it is to be understood that agents appropriate to generate other ester derivatives are anticipated by these examples and therefore should be considered as a simple derivative of the methods disclosed herein. (e.g., substitution of ethanol or propanol for methanol)

Materials and Methods

Hexane (OmniSolv™) was purchased from EM Science, Chemy Hill, N.Y. Absolute methanol and potassium hydroxide were obtained from J. T. Baker Chemical Co., Phillipsburg, N.J. Chloroform and sulfuric acid were purchased from Fisher Scientific, Tustin, Calif. Sodium methoxide and boron trifluoride-methanol were obtained from Sigma-Aldrich, St. Louis, Mo. The Supelco™ standard FAME mixture (47885-U) was obtained from Supelco™, Bellefonte, Pa. Spring Valley fish oil capsules were distributed by Leiner Health Products, Carson, Calif. Tonalin 1000-CLA (conjugated linoleic acid) capsules were obtained from Nature Bounty, Bohemia, N.Y. All other fatty acid standards were purchased from Nu-Chek™ Prep. Inc., Elysian, Minn. Beef longissimus muscle samples were obtained from department owned animals processed at an abattoir. Nuts and sundry food items were purchased from local grocery stores. Coffee bean grinders were purchased from Mr. Coffee™, Inc., Cleveland, Ohio. Pyrex™ screw-cap culture tubes (16×125 mm) were obtained from Corning Laboratory Science Company, Corning, N.Y. The Tekmar™ VXR-10 multi-tube vortex was purchased from Jenke and Kunkel, West Germany.

Direct FAME Synthesis

Samples were uniformly distributed by grinding for 10-15 sec in a room-temperature coffee bean grinder. Samples could be processed in the state obtained, e.g., wet, dry, freeze-dried, or semi-frozen. Samples (0.5 g wet, dry, or semi-frozen sample), (0.25 g freeze-dried sample), or oils (20 µl) were placed into a 16×125 mm screw-cap Pyrex culture tube to which 1.0 ml C13:0 internal standard (0.5 mg C13:0/ml methanol), 0.7 ml 10 N KOH in water, and 5.3 ml methanol was added. The tube was incubated in a 55° C. water bath for 1.5 h with vigorous 5 sec hand-shaking every 20 min to properly permeate, dissolve and hydrolyze the sample. After cooling below room temperature in a cold tap water bath, 0.58 ml of 24 N $H_2SO_4$ in water was added. (Care is taken in the preparation of the stock solutions 10 N KOH and 24 N $H_2SO_4$, especially as the $H_2SO_4$ solution is extremely exothermic.) The tube was mixed by inversion, and with precipitated $K_2SO_4$ present, was incubated again in a 55° C. water bath for 1.5 h with 5 sec hand-shaking every 20 min. After FAME synthesis, the tube was cooled in a cold tap water bath. Three ml of hexane was added and the tube was vortex-mixed for 5 min on a multi-tube vortex. The tube was centrifuged for 5 min in a tabletop centrifuge and the hexane layer, containing the FAME, was placed into a gas chromatography (GC) vial. The vial was capped and placed at −20° C. until GC analysis.

FAME Synthesis with Sodium Methoxide or Boron Trifluoride

Freeze-dried tissue samples were uniformly distributed by grinding for 10-15 sec in a room-temperature coffee bean grinder. Samples of freeze-dried tissue (0.25 g), or oils (20 µl) were placed into a 16×125 mm screw-cap Pyrex™ culture tube to which 1.0 ml methyl C13:0 internal standard (0.5 mg methyl C13:0/ml methanol) was added. Two ml of sodium methoxide (0.5 M) or 2 ml of boron trifluoride in methanol (14%, wt/vol) were added to the Pyrex tubes containing the samples. The tubes were incubated in a 55° C. water bath for 1.5 h with vigorous 5 sec hand-shaking every 20 min. Two ml of a saturated solution of $NaHCO_3$ and 3 ml hexane were then added and the tubes were vortex-mixed. After centrifugation, the hexane layer containing the FAME was placed into a GC vial. The vial was capped and placed at −20° C. until GC analysis.

Gas Chromatography

The fatty acid composition of the FAME was determined by capillary gas chromatography on a SP™-2560, 100 m×0.25 mm×0.20 µm capillary column (Supelco™, Bellefonte, Pa.) installed on a Hewlett Packard 5890 gas chromatograph equipped with a Hewlett Packard 3396 Series II integrator and 7673 controller, a flame ionization detector and split injection. Initial oven temperature was 140° C., held for 5 min, subsequently increased to 240° C. at a rate or 4° C. $min^{-1}$, and then held for 20 min. Helium was used as the carrier gas at a flow rate of 0.5 ml $min^{-1}$, column head pressure was 40 psi. Both the injector and detector were set at 260° C. The split ratio was 30:1. Fatty acids were identified by comparing their retention times with fatty acid methyl standards described under Materials.

Statistical Analysis

Duplicate gas chromatograph results were averaged for animal and methylation method. ANOVA was determined using a model with methylation method as the treatments and animal as a blocking factor in a randomized complete block design. When the F-ratio for the methylation methods was significant, Student's t-test was used to make pairwise comparisons among the data sets.

Example 2

Sodium Methoxide, Boron Trifluoride, and Direct FAME Synthesis Methods Applied to a Supelco™ Standard FAME Mixture For an initial FAME synthesis analysis, we used a Supelco™ standard FAME mixture. This standard mixture contained FAME in a defined ratio, and consisted of both short and long chain saturated, monounsaturated, and polyunsaturated fatty acids. In order to broadly assess certain features of our method, we compared the results of direct FAME synthesis to those of the base catalyst sodium methoxide and the acid catalyst boron trifluoride.

Direct FAME synthesis, as described in Materials and Methods, is a two-step procedure. In the first step, sample fatty acid esters are hydrolyzed to free fatty acid anions and in the second step the free fatty acid anions are converted to FAME. When the first step of direct FAME synthesis was applied to the Supelco™ standard FAME mixture, the esters were hydrolyzed to free fatty acid anions that were not volatile enough to enter the GC column. These results, i.e., the absence of fatty acid peaks, provided formal evidence that the first step in direct FAME synthesis completely hydrolyzed the Supelco standard FAME to free fatty acid anions which was the desired general prerequisite for the subsequent methylation step of direct FAME synthesis (data not shown).

When the second step of direct FAME synthesis, the methylation step, was applied to the Supelco™ free fatty acid anions produced by the first step, the results shown in Table 1 were obtained. All of the GC peaks present in the original Supelco™ standard mixture were again observed, as can be seen by comparing the fatty acids of direct FAME synthesis to those of the Supelco™ mix. When presented with a FAME sample, as in this experiment, both sodium methoxide and boron trifluoride likewise gave the same FAME values present in the original Supelc™ mix (Table 1).

Fatty acid artifacts, e.g., the conversion of CLA to other isomers, are a concern in fatty acid analysis (Kramer et al. 1997; Park et al., 2002; Shahin et al., 2003). Since direct FAME synthesis did not generate new fatty acid peaks, no fatty acid artifacts were created in the Supelco standard FAME mixture.

Example 3

The Methods of Sodium Methoxide, Boron Trifluoride, and Direct FAME Synthesis Applied to Fish Oil A comparison was made between the base catalyst sodium methoxide, the acid catalyst boron trifluoride, and direct synthesis, on FAME production from fish oil commercially obtained as a human nutritional supplement. The results are shown in Table 2.

Twenty fatty acids were identified in the fish oil sample. Direct FAME synthesis recovered more total amount of fatty acid than did either of the other two methods as would be expected if direct FAME synthesis generated methyl esters of all the fatty acids in the sample. In comparison, base catalysis with sodium methoxide methylated esterified fatty acids, but not free fatty acid anions (Kramer et al., 1997), whereas, acid catalysis by boron trifluoride should have methylated all fatty acids, including esterified, unesterified, and those in salt form (Carrapiso and Garcia, 2000).

In analyzing the total fatty acids methylated, direct FAME synthesis converted 22% more fatty acids to FAME than did sodium methoxide and 14% more than did boron trifluoride indicating that there must be groups of fatty acids present that the latter two methods did not recognize. Such limitations with these two reagents have been previously noted (Kramer et al., 1997; Christie, 2003). The direct FAME synthesis method apparently methylates all of the fatty acids present, which explains why the direct FAME synthesis recoveries were higher than the other two methods.

When the peak areas were expressed as % of total fatty acid (% FA) present by each method, the % FAs were similar for all three methods even though total recovery among the three methods was somewhat different. This indicates that the fatty acids not methylated by sodium methoxide or boron trifluoride were present in similar ratios for all of the fatty acids present. The results with sodium methoxide, which does not methylate free fatty acid anions, indicates that because it methylated only 82% of the total fatty acids present the other 18% of the fatty acids present may have been free fatty acid anions.

Example 4

Conjugated Linoleic Acid Analysis Using Sodium Methoxide, Boron Trifluoride or Direct Synthesis Table 3 presents the results obtained from an analysis of commercial CLA capsules using sodium methoxide, boron trifluoride and direct synthesis. The CLA capsules contained the two important CLA isomers C18:2c9,t11 and C18:2t10, c12, and also palmitic (C 16:0), stearic (C18:0), oleic (C18:1n9), and linoleic (C18:2n6) fatty acids.

Most notable, was the difference in the results obtained with sodium methoxide compared to that obtained with boron trifluoride and direct FAME synthesis. Only 0.4% of the fatty acids present were methylated by sodium methoxide, indicating that they were all free fatty acid anions, and not esterified. As noted previously, sodium methoxide methylates esterified fatty acids, but not free fatty acid anions (Kramer et al., 1997). This example serves as a caution that a researcher who uses sodium methoxide, or alkaline catalysts in general, is at great risk of missing fatty acids, whereas, direct FAME synthesis methylates all of the fatty acids present.

Boron trifluoride and direct FAME synthesis gave essentially the same results for the fatty acids present in the CLA capsules. Once again, the direct FAME synthesis method did not generate fatty acid artifacts, including CLA artifacts, as all of the peaks were essentially identical to those of the boron trifluoride method. The absence of CLA artifacts confirmed the work of Park et al. (2002), who used similar $H_2SO_4$ conditions on CLA samples as was used with direct FAME synthesis, but Park et al (2002) did not have water present.

Example 5

The Analysis of Beef Longissimus Muscle Using Sodium Methoxide, Boron Trifluoride or Direct FAME Synthesis The analysis of freeze-dried beef longissimus muscle fatty acids using sodium methoxide, boron trifluoride and direct FAME synthesis is presented in Table 4. Once again, there were striking differences among the three methods. Direct FAME synthesis recovered more fatty acids than did sodium methoxide and much more than did boron trifluoride. Since most of the fatty acids were esterified in longissimus muscle, as opposed to unesterified in the CLA capsule (Table 3), it was not surprising that sodium methoxide performed much better in FAME synthesis of this sample, although it methylated only 78% of the fatty acids present. This sample also shows that boron trifluoride performed much better with the free fatty acid anions in the CLA sample (Table 3) than with the esterified fatty acids in muscle tissue. This latter result was surprising since boron trifluoride can methylate all families of fatty acids (Carrapiso and Garcia, 2000). Although boron trifluoride did methylate all of the different fatty acids present, as all of the peaks were identical to direct FAME synthesis, it did not do so quantitatively. It is unclear at this time why boron trifluoride gave such poor results. It can be mentioned that Bolte et al. reports satisfactory FAME synthesis results using boron trifluoride on freeze-dried lamb muscle tissue fatty acids by using much higher temperature and more concentrated effort, i.e., by incubating at 80° C. and vortex-mixing two to three times/min. However, our results do not seem to be due to the fact that boron trifluoride cannot permeate the meat sample, because similar results were observed when using a chloroform:methanol extract according to the method of Folch et al. (1956), where extraction of fatty acids by boron trifluoride would no longer be an issue (data not shown). Apparently, and unexpectedly, there are fatty acid structures in beef longissimus muscle that can be easily methylated by direct synthesis but not by boron trifluoride.

When expressed as % FA, sodium methoxide and direct FAME synthesis were quite similar in their results, but boron trifluoride was different, and in this latter case the % FA values were higher when the concentration of fatty acid was lower. This difference could be explained by the fact that boron trifluoride methylated only 46% of the fatty acids present in longissimus muscle, and did so preferentially. With boron trifluoride, long chain unsaturated fatty acids appeared to be methylated more efficiently than short chain or saturated fatty acids, whereas, direct FAME synthesis methylated fatty acids without bias to chain length or structure. As a result, direct FAME synthesis consistently methylated more fatty acid, averaging 1.3 times that of sodium methoxide and 2.2 times that of boron trifluoride.

Example 6

Independent Assessment of Direct FAME Synthesis Efficiency

To determine if the direct FAME synthesis could extract all of the fatty acids present in beef longissimus muscle, we independently compared it to the LECO™ TFE2000 Fat Extractor™ (LECO™ Corporation, St. Joseph, Mich.). These results are shown in Table 5. For the analysis of this experiment, wet tissue and freeze dried tissue was corrected to a dry matter basis. Direct FAME synthesis, whether applied to dry or wet muscle tissue, extracted all of the fatty acids present when compared to the LECO™ TFE200 Fat Extractor™, assuming that the LECO™ values should be 6-9% higher since the LECO™ values also contain glycerol and cholesterol. In this respect, direct synthesis gives a truer value of fat content then does the LECO™ extractor, which does not differentiate fatty acids from total lipid.

Example 7

Direct FAME Synthesis Applied to Wax Esters, Cholesteryl Derivatives, and Fatty Acid Salts The ideal FAME synthesis method would be able to analyze fatty acids from samples of wax esters, cholesteryl lipid derivatives, and alkyl methane sulfonates (Palmquist and Jenkins, 2003). We applied the direct FAME synthesis method to such families of fatty acids and the results are shown in Table 6. Direct FAME synthesis was able to identify the fatty acids in wax esters as represented by palmityl stearate (saturated series) and stearyl linoleate (unsaturated series), cholesteryl lipid derivatives as represented by cholesteryl oleate, and fatty acid salts, as represented by oleyl methane sulfonate. As the second component in each of these compounds was a fatty alcohol, and not a fatty acid, it was not converted to the FAME. This is as it should be, since we were analyzing strictly for fatty acid components. Depending on the concentration of these very hydrophobic families of fatty acids, full quantification might require more shaking and a longer incubation time during the first step of direct FAME synthesis.

Example 8

Effect of Water Content on FAME Production by Direct FAME Synthesis

Figure 1:
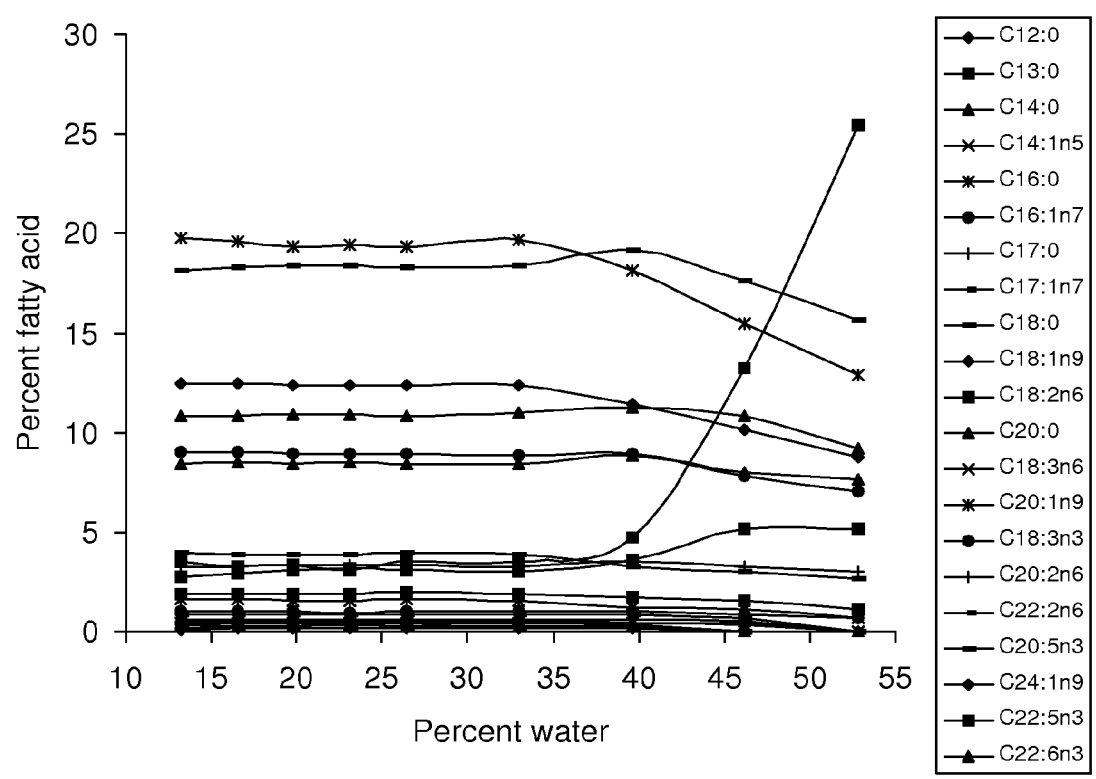
FIG. 1 shows the effect of water concentration on fatty acid methyl ester (FAME) production of fish oil fatty acids by direct FAME synthesis.

It is of great interest to know what the limiting concentration of water might be for the direct FAME synthesis method. There has to be such a limit, for no other reason than the fact there has to be a certain concentration of methylating reagents. In FIG. 1, we show the effect of water concentration on the direct FAME synthesis method. As the percentage of water was increased, the total amount of fatty acids methylated decreased (data not shown), but this was easily corrected for by the internal standard. Most importantly, the percentage of each fatty acid remained constant up to 33% water. Only above 33% water do the FAME production results become problematic. In comparison, our reagents, without any sample present, constitute only 13% water in a final reaction volume of 7.58 ml. Thus, from a practical standpoint, one can replace 1.5 ml of MeOH with a 1.5 ml aqueous sample for a final concentration of 33% water. For example, using the protocol as given, 1.5 ml of milk can be analyzed directly by our method.

Example 9

The Versatility of Direct FAME Synthesis

Figure 2:
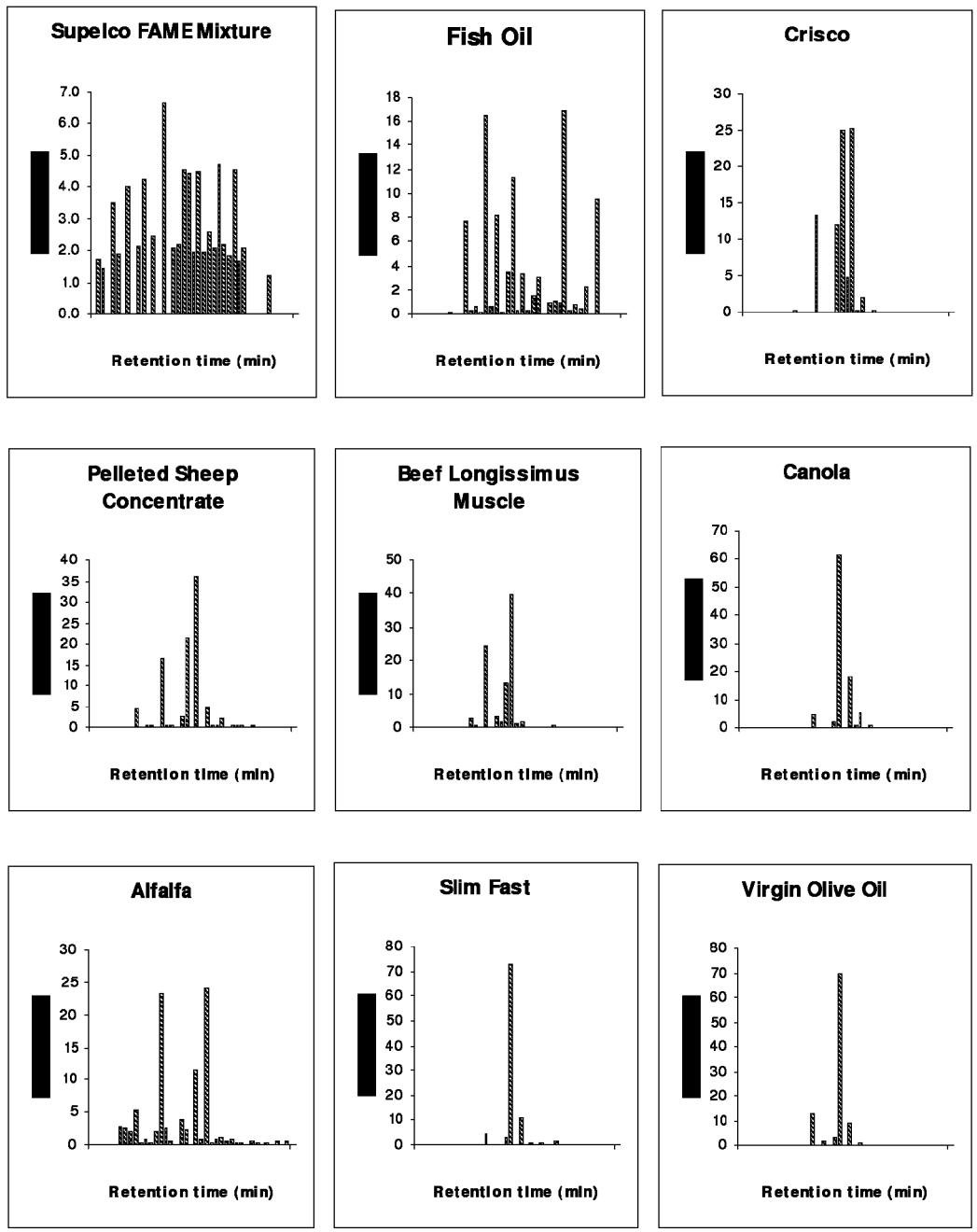
FIG. 2 shows direct FAME synthesis from samples of Supelco™ FAME mixture, fish oil, Crisco™, pelleted sheep concentrate, beef longissimus muscle, canola, alfalfa, Slim Fast™, and virgin olive oil, where % Fatty acid=% of total fatty acid present in sample.
Figure 3:
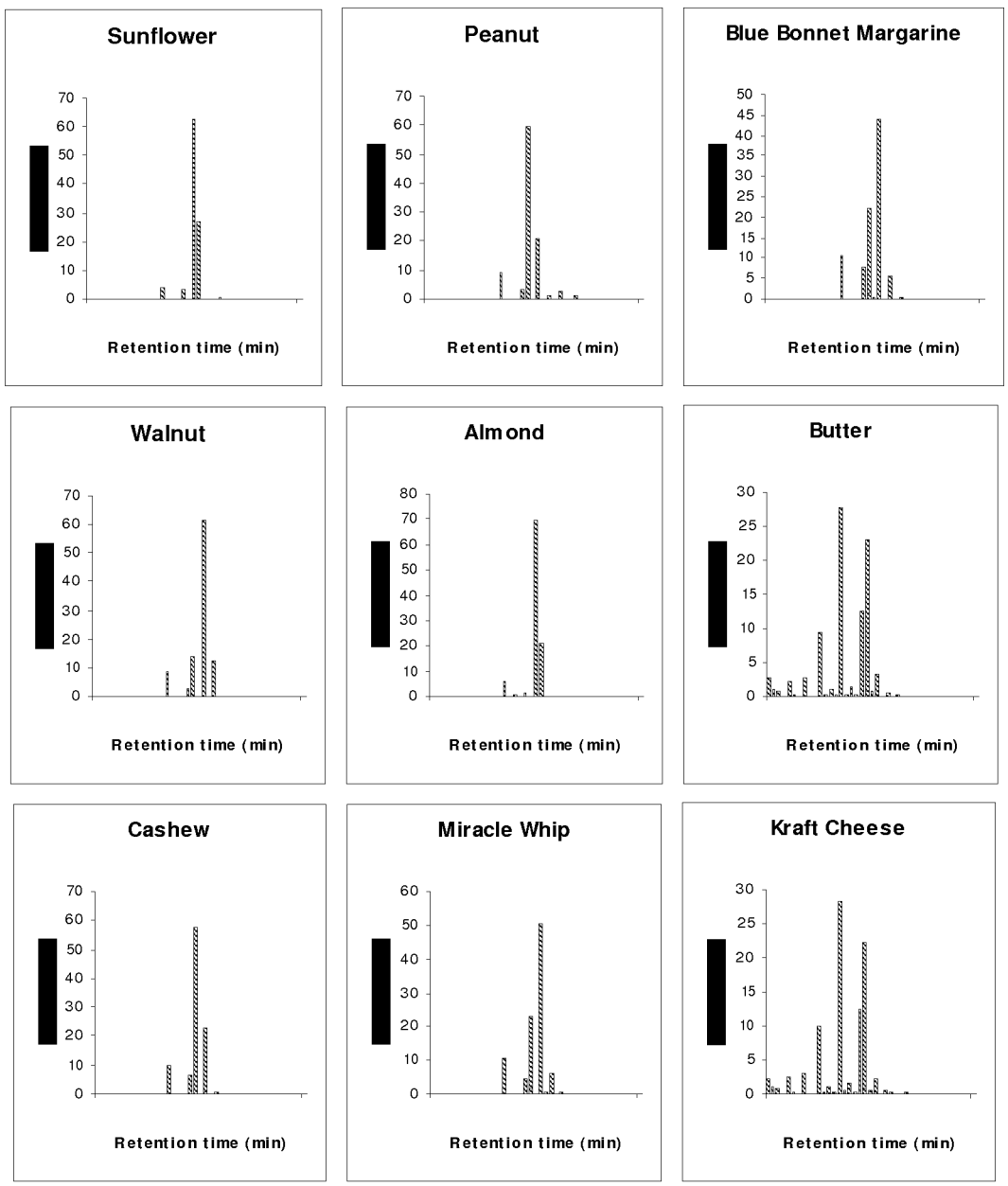
FIG. 3 shows direct FAME synthesis from samples of sunflower seeds, peanuts, Blue Bonnet™ margarine, walnuts, almonds, butter, cashews, Miracle Whip™, and Kraft American™ processed cheese, where % Fatty acid=% of total fatty acid present in sample.

The ideal method for the analysis of fatty acids would be applicable to any sample whose fatty acid content was desired. With this in mind, direct FAME synthesis was applied to various products and the results are shown in FIGS. 2 and 3. We evaluated a number of oil sources including fish, Canola, and virgin olive; a number of nuts including almond, cashew, peanut, sunflower, and walnut; a couple of feedstuffs, including pelleted sheep concentrate and alfalfa; and foodstuffs including beef longissimus muscle, butter, cheese, Crisco™, margarine, Miracle Whip™, and Slim Fast™. The direct FAME synthesis method readily generated a FAME profile for all of these different samples.

When % FA was plotted against retention time and presented as in FIGS. 2 and 3, it was instantly seen that each sample has its own 'fatty acid print'. Most samples were dominated by 1 to 3 fatty acids, i.e., 1 to 3 fatty acids accounted for 85%, or more, of the total fatty acid composition of the sample. When the graphs were arrayed as they were in these two figures, it was easy to visually compare one sample to another, e.g., the vegetable oil product Crisco™ contained 25% oleic and 25% linoleic fatty acids, while olive oil contained 70% oleic acid; beef longissimus muscle contained 40% oleic and 25% palmitic acids, while Slim Fast™ contained 70% oleic acid of the total fatty acids present. The dairy products, butter and Kraft American™ processed cheese, had very similar fatty acid profiles. The fatty acid composition of the foods presented in FIGS. 2 and 3 are in very good agreement with the fatty acid tabulations in handbooks (Watt, 1975; McCance, 2002).

Even though certain fatty acids have limited solubility in water/methanol, hydrolysis of fatty acid esters still occurs at the water/methanol:lipid interface and can, in fact, be accounted for by the internal standard. For concentrated fat solutions, and waxes, the hydrolysis step might take longer than 1.5 h at 55° C. to complete. All of our results show the efficacy of the direct FAE synthesis method, which allows up to 33% water content (e.g., see FIG. 2). KOH in MeOH alone could not solubilize and permeate tissues as well as when water was added, and $H_2SO_4$ in MeOH precipitated tissues, rather than solubilized them.

Of further interest were the results obtained by direct FAME synthesis when compared, in various situations, to the sodium methoxide and boron trifluoride methods. Most striking was the case of CLA analysis (Table 3) where sodium methoxide could not methylate any CLA in a capsule full of it. Similarly, but not so pronounced, was the fact that boron trifluoride methylated only 46% of the fatty acids present in beef longissimus muscle (Table 4). In the latter instance, expressing the results as % FA could mask the inadequacies of the method, but at a closer examination this too would fail. If a method results in a differential extraction and synthesis of FAME, then at some point the % FA will be wrong. Such an example can be found with the boron trifluoride results in Table 4. The concentration of C20:4n6 in beef longissimus muscle was 1.6% with the boron trifluoride method, but only 0.9% with the direct FAME synthesis method. This two fold discrepancy was accounted for by the fact that boron trifluoride differentially methylated a higher percentage of C20:4n6 than it did of other fatty acids present. Direct FAME synthesis provided the most accurate values because it methylated all of the fatty acids present in beef longissimus muscle (Table 4) as verified by an independent analysis with the LECO™ TFE2000 Fat Extractor™ (Table 5).

Table 7, provides a comparison of sodium methoxide, direct FAME synthesis, and $BF_3$ FAE synthesis methods on a variety of low value, high fat organic materials. Direct FAME synthesis methylated all of the fatty acids in all of the oils tested with a high degree of recovery. The 95% recovery in the two grease samples could easily be explained if these two samples contained 5% water by weight (we expect water in this type of sample).

What was a real surprise, were the unsatisfactory results obtained with sodium methoxide. The results were expected to be much better, especially in the pure oil samples of soy, canola, and corn. The sodium methoxide is notorious it's inability to methylate free fatty acid anions, as transesterification requires an ester of some sort. All of the samples here were rather old and could be degraded with free fatty acid anions (actually expected in the greases), and free fatty acid anions themselves also inhibit transesterification. On the other hand, is known that sodium methoxide is not all that efficient in its reaction. It is known as a major drawback in the biodiesel industry, that transesterification leaves unreacted molecules in mono- and diglycerides that increase the viscosity of the biodiesel produced. Lastly, as all of the samples were old, they might have absorbed some water, and transesterification cannot survive even small concentrations of water.

To validate the quality of the sodium methoxide, we compared sodium methoxide to direct synthesis on a fresh corn oil sample. In this experiment, the concentration of oil was 20 times higher than that normally used. As can be seen in table 7, both methods methylated the oil with a high yield. With the fresh oil, the sodium methoxide method experienced ideal conditions and was successful in biodiesel production.

TABLE 1

Effect of sodium methoxide, boron trifluoride or direct FAME synthesis on a standard Supelco ™ FAME mixture

| Fatty acid | Structure | Supelco ™ Mix mg/g | SD[a] | Methoxide mg/g | SD[a] | $BF_3$ mg/g | SD[a] | Direct synthesis mg/g | SD[a] |
|---|---|---|---|---|---|---|---|---|---|
| Capric | C10:0 | 40.02 | 0.28 | 38.93 | 0.29 | 39.91 | 0.55 | 39.40 | 0.24 |
| Undecanic | C11:0 | 20.41 | 0.25 | 19.77 | 0.17 | 20.00 | 0.00 | 20.23 | 0.03 |
| Lauric | C12:0 | 39.57 | 0.36 | 38.66 | 0.14 | 39.06 | 0.28 | 39.01 | 0.39 |
| Tridecanic | C13:0 | 20.80 | 0.02 | 20.34 | 0.27 | 20.69 | 0.07 | 20.71 | 0.05 |
| Myristic | C14:0 | 41.12 | 0.16 | 39.43 | 0.35 | 40.84 | 0.34 | 40.91 | 0.41 |
| Myristoleic | C14:1n5 | 20.38 | 0.32 | 18.53 | 0.17 | 19.88 | 0.05 | 20.05 | 0.01 |
| Pentadecanoic | C15:0 | 21.54 | 0.05 | 20.62 | 0.39 | 21.09 | 0.25 | 21.16 | 0.22 |
| Pentadecenoic | C15:1n5 | 20.60 | 0.22 | 18.90 | 0.25 | 20.47 | 0.29 | 20.22 | 0.07 |
| Palmitic | C16:0 | 63.25 | 0.52 | 62.99 | 0.78 | 63.04 | 0.35 | 62.90 | 0.07 |
| Palmitoleic | C16:1n7 | 20.86 | 0.15 | 20.07 | 0.15 | 20.83 | 0.09 | 21.07 | 0.14 |
| Heptadecanoic | C17:0 | 18.66 | 0.55 | 21.42 | 0.21 | 18.62 | 0.08 | 21.23 | 0.36 |
| Heptadecenoic | C17:1n7 | 21.29 | 0.07 | 20.93 | 0.57 | 21.42 | 0.12 | 21.57 | 0.20 |
| Stearic | C18:0 | 42.68 | 0.25 | 43.72 | 0.64 | 42.66 | 0.52 | 42.97 | 0.35 |
| Elaidic | C18:1n9t | 21.85 | 0.01 | 22.57 | 1.43 | 21.67 | 0.03 | 21.58 | 0.08 |
| Oleic | C18:1n9 | 43.06 | 0.27 | 43.78 | 1.37 | 43.58 | 0.26 | 42.70 | 0.08 |
| Linolelaidic | C18:2n6t | 20.15 | 0.19 | 19.92 | 0.13 | 20.02 | 0.51 | 20.26 | 0.05 |
| Linoleic | C18:2n6 | 20.89 | 0.14 | 20.25 | 0.61 | 20.87 | 0.11 | 20.58 | 0.10 |
| Arachidic | C20:0 | 41.68 | 0.20 | 42.50 | 0.13 | 41.61 | 0.74 | 42.32 | 0.10 |
| Gamma- Linolenic | C18:3n6 | 19.54 | 0.07 | 18.36 | 0.02 | 19.12 | 0.05 | 19.50 | 0.18 |
| Eicosenoic | C20:1n9 | 21.06 | 0.11 | 21.08 | 0.01 | 20.62 | 0.06 | 20.87 | 0.15 |
| Linolenic | C18:3n3 | 19.84 | 0.25 | 18.69 | 0.15 | 20.33 | 0.25 | 19.92 | 0.19 |
| Heneicosanoic | C21:0 | 21.62 | 0.35 | 21.98 | 0.10 | 21.77 | 0.08 | 21.66 | 0.34 |
| Eicosadienoic | C20:2 | 20.44 | 0.07 | 20.30 | 0.16 | 20.65 | 0.08 | 19.85 | 0.67 |
| Behenic | C22:0 | 42.20 | 0.08 | 43.27 | 0.66 | 42.18 | 0.04 | 41.91 | 0.16 |
| Eicosatrienoic | C20:3n6 | 19.49 | 0.03 | 19.36 | 0.00 | 20.08 | 0.12 | 19.26 | 0.06 |
| Erucic | C22:1n9 | 19.86 | 0.58 | 20.88 | 0.13 | 19.40 | 0.36 | 19.05 | 0.22 |
| Eicosatrienoic | C20:3n3 | 18.50 | 0.03 | 18.82 | 0.21 | 20.47 | 0.48 | 19.51 | 0.13 |
| Arachidonic | C20:4n6 | 18.52 | 0.46 | 19.38 | 0.07 | 18.94 | 0.06 | 18.71 | 0.22 |
| Tricosanoic | C23:0 | 18.54 | 0.49 | 19.25 | 0.07 | 18.86 | 0.05 | 18.67 | 0.20 |
| Docosadienoic | C22:2n6 | 19.16 | 0.39 | 19.86 | 0.37 | 19.23 | 0.06 | 19.09 | 0.04 |
| Lignoceric | C24:0 | 34.34 | 1.45 | 37.72 | 0.31 | 31.84 | 0.70 | 32.00 | 0.22 |
| Eicosapentaenoic | C20:5n3 | 19.58 | 2.10 | 17.60 | 0.23 | 22.29 | 0.11 | 23.21 | 0.28 |
| Nervonic | C24:1n9 | 17.04 | 0.12 | 18.53 | 0.31 | 16.74 | 0.76 | 16.13 | 0.18 |
| Docosahexaenoic | C22:6n3 | 11.48 | 0.50 | 11.60 | 0.17 | 11.24 | 0.16 | 11.82 | 0.08 |
| Total | | 880.02 | 10.56 | 880.01 | 10.55 | 880.02 | 7.51 | 880.03 | 6.00 |

[a]SD = Standard deviation. Three Supelco FAME standard vials were pooled and then divided into two separate samples for methylation as described in Materials and Methods.

TABLE 2

Fish oil FAME synthesis by sodium methoxide, boron trifluoride or direct FAME synthesis

| Fatty acid | Structure | Sodium methoxide | | | Boron trifluoride | | | Direct synthesis | | |
|---|---|---|---|---|---|---|---|---|---|---|
| | | mg/g | SD[a] | % FA[b] | mg/g | SD[a] | % FA[b] | mg/g | SD[a] | % FA[b] |
| Lauric | C12:0 | 1.01 | 0.05 | 0.2 | 1.14 | 0.11 | 0.2 | 1.01 | 0.11 | 0.1 |
| Myristic | C14:0 | 55.74 | 2.93 | 9.0 | 61.53 | 1.80 | 9.2 | 66.69 | 3.33 | 8.8 |
| Myristoleic | C14:1n5 | 3.86 | 0.20 | 0.6 | 4.25 | 0.13 | 0.6 | 4.70 | 0.29 | 0.6 |
| Palmitic | C16:0 | 126.54 | 6.66 | 20.4 | 134.06 | 3.15 | 20.1 | 155.95 | 8.34 | 20.5 |
| Palmitoleic | C16:1n7 | 59.02 | 3.11 | 9.5 | 63.66 | 1.81 | 9.5 | 70.95 | 3.50 | 9.3 |
| Heptadecanoic | C17:0 | 3.33 | 0.18 | 0.5 | 3.40 | 0.07 | 0.5 | 4.11 | 0.28 | 0.5 |
| Heptadecenoic | C17:1n7 | 1.13 | 0.06 | 0.2 | 1.22 | 0.06 | 0.2 | 1.35 | 0.07 | 0.2 |
| Stearic | C18:0 | 25.17 | 1.32 | 4.1 | 25.66 | 0.50 | 3.8 | 31.18 | 1.60 | 4.1 |
| Oleic | C18:1n9 | 81.31 | 4.28 | 13.1 | 85.95 | 2.55 | 12.9 | 98.36 | 4.90 | 12.9 |
| Linoleic | C18:2n6 | 20.54 | 1.08 | 3.3 | 19.79 | 0.67 | 3.0 | 21.35 | 0.85 | 2.8 |
| Arachidic | C20:0 | 1.83 | 0.10 | 0.3 | 1.71 | 0.01 | 0.3 | 2.43 | 0.16 | 0.3 |
| Gamma- Linolenic | C18:3n6 | 2.70 | 0.14 | 0.4 | 3.11 | 0.06 | 0.5 | 3.27 | 0.18 | 0.4 |
| Eicosenoic | C20:1n9 | 10.43 | 0.55 | 1.7 | 10.06 | 0.04 | 1.5 | 12.83 | 0.66 | 1.7 |
| Linolenic | C18:3n3 | 6.71 | 0.35 | 1.1 | 7.16 | 0.22 | 1.1 | 8.04 | 0.40 | 1.1 |
| Eicosadienoic | C20:2n6 | 21.67 | 1.14 | 3.5 | 23.62 | 0.77 | 3.5 | 25.43 | 1.11 | 3.3 |
| Docosadienoic | C22:2n6 | 5.57 | 0.29 | 0.9 | 5.85 | 0.19 | 0.9 | 6.71 | 0.33 | 0.9 |
| Eicosapentaenoic | C20:5n3 | 117.67 | 6.19 | 18.9 | 127.90 | 3.22 | 19.2 | 142.59 | 6.82 | 18.8 |
| Nervonic | C24:1n9 | 2.22 | 0.12 | 0.4 | 2.46 | 0.08 | 0.4 | 3.10 | 0.11 | 0.4 |
| Docosapentaenoic | C22:5n3 | 12.37 | 0.65 | 2.0 | 12.51 | 0.12 | 1.9 | 14.67 | 0.73 | 1.9 |
| Docosahexaenoic | C22:6n3 | 62.43 | 3.29 | 10.0 | 71.86 | 0.75 | 10.8 | 85.27 | 4.06 | 11.2 |
| Total | | 621.23 | 32.70 | 100.0 | 666.89 | 16.13 | 100.0 | 760.00 | 37.63 | 100.0 |

[a]SD = Standard deviation. Three fish oil capsules were pooled and then divided into two separate samples for methylation as described in Materials and Methods.
[b]% FA = % of total fatty acids identified in sample.

TABLE 3

Conjugated linoleic acid (CLA) FAME synthesis by sodium methoxide, boron trifluoride or direct FAME synthesis

| Fatty acid | Structure | Sodium methoxide | | Boron trifluoride | | Direct synthesis | |
|---|---|---|---|---|---|---|---|
| | | mg/g | SD[a] | mg/g | SD[a] | mg/g | SD[a] |
| Palmitic | C16:0 | nd[b] | | 14.82 | 1.35 | 13.37 | 1.22 |
| Stearic | C18:0 | nd[b] | | 24.78 | 1.49 | 24.25 | 2.45 |
| Oleic | C18:1n9 | nd[b] | | 111.97 | 5.46 | 108.78 | 10.24 |
| Linoleic | C18:2n6 | nd[b] | | 3.32 | 0.15 | 3.25 | 0.34 |
| c9,t11 CLA | C18:2c9, t11 | 1.35 | 0.12 | 295.08 | 13.91 | 311.90 | 40.40 |
| t10,c12 CLA | C18:2t10, c12 | 1.45 | 0.21 | 289.44 | 11.92 | 308.45 | 37.25 |
| Total | | 2.81 | 0.33 | 739.42 | 34.27 | 770.00 | 91.90 |

[a]SD = Standard deviation. Three CLA capsules were pooled and then divided into two samples for methylation as described in Materials and Methods.
[b]nd = Not detected.

TABLE 4

Beef Longissimus muscle FAME synthesis by sodium methoxide, boron trifluoride or direct FAME synthesis

| Fatty acid | Structure | Sodium methoxide | | Boron trifluoride | | Direct synthesis | |
|---|---|---|---|---|---|---|---|
| | | mg/g[a] ± SE[b] | % FA[c] | mg/g[a] ± SE[b] | % FA[c] | mg/g[a] ± SE[b] | % FA[c] |
| Lauric | C12:0 | 0.21 ± 0.02[d] | 0.09[d] | 0.17 ± 0.01[d] | 0.12[e] | 0.24 ± 0.02[e] | 0.08[d] |
| Myristic | C14:0 | 8.34 ± 0.68[e] | 3.46[e] | 5.57 ± 0.25[d] | 3.90[f] | 10.29 ± 0.83[f] | 3.32[d] |
| Myristoleic | C14:1n5 | 2.01 ± 0.14[e] | 0.83[e] | 1.38 ± 0.08[d] | 0.97[f] | 2.29 ± 0.21[e] | 0.74[d] |
| Pentadecanoic | C15:0 | 1.59 ± 0.14[d] | 0.66[d] | 1.24 ± 0.08[d] | 0.87[f] | 2.23 ± 0.18[e] | 0.72[e] |
| Palmitic | C16:0 | 62.82 ± 4.10[e] | 26.07[d] | 38.00 ± 0.86[d] | 26.61[e] | 80.85 ± 4.84[f] | 26.08[d] |
| Palmitoleic | C16:1n7 | 8.10 ± 0.65[e] | 3.36[d] | 5.74 ± 0.19[d] | 4.02[e] | 10.91 ± 0.66[f] | 3.52[e] |
| Heptadecanoic | C17:0 | 3.89 ± 0.35[d] | 1.61[e] | 2.03 ± 0.08[d] | 1.42[d] | 5.05 ± 0.37[f] | 1.63[e] |
| Stearic | C18:0 | 30.25 ± 1.89[d] | 12.56[e] | 15.55 ± 0.28[d] | 10.89[d] | 39.25 ± 2.31[f] | 12.66[e] |
| t-Vaccenic | C18:1n11t | 19.20 ± 2.36[e] | 7.97[f] | 9.35 ± 0.96[d] | 6.55[e] | 22.21 ± 3.28[e] | 7.16[e] |
| Oleic | C18:1n9 | 87.10 ± 5.28[e] | 36.15[e] | 47.60 ± 1.03[d] | 33.34[d] | 113.91 ± 6.43[f] | 36.75[e] |
| Linoleic | C18:2n6 | 10.70 ± 0.62[d] | 4.44[d] | 10.50 ± 0.46[d] | 7.36[e] | 13.98 ± 0.82[e] | 4.51[d] |
| Arachidic | C20:0 | 0.60 ± 0.06[f] | 0.25[f] | 0.00 ± 0.00[d] | 0.00[d] | 0.40 ± 0.05[e] | 0.13[e] |
| Gamma- Linolenic | C18:3n6 | 0.32 ± 0.03[e] | 0.13[e] | 0.17 ± 0.02[d] | 0.12[d] | 0.28 ± 0.02[e] | 0.09[d] |
| Eicosenoic | C20:1n9 | 0.20 ± 0.01[e] | 0.08[d] | 0.10 ± 0.00[d] | 0.07[d] | 0.64 ± 0.05[f] | 0.21[e] |
| Linolenic | C18:3n3 | 0.56 ± 0.04[e] | 0.23[e] | 0.21 ± 0.01[d] | 0.15[d] | 0.91 ± 0.05[f] | 0.29[f] |
| c-9,t-11 CLA | C18:2c9,t11 | 0.70 ± 0.04[e] | 0.29[e] | 0.59 ± 0.02[d] | 0.41[e] | 0.85 ± 0.09[f] | 0.27[d] |
| Eicosadienoic | C20:2 | 0.25 ± 0.02[e] | 0.10[e] | 0.17 ± 0.01[d] | 0.12[e] | 0.20 ± 0.02[e] | 0.06[d] |
| Behenic | C22:0 | 0.40 ± 0.04[f] | 0.17[e] | 0.25 ± 0.02[e] | 0.18[e] | 0.18 ± 0.01[d] | 0.06[d] |

TABLE 4-continued

Beef Longissimus muscle FAME synthesis by sodium methoxide, boron trifluoride or direct FAME synthesis

| Fatty acid | Structure | Sodium methoxide | | Boron trifluoride | | Direct synthesis | |
|---|---|---|---|---|---|---|---|
| | | mg/g[a] ± SE[b] | % FA[c] | mg/g[a] ± SE[b] | % FA[c] | mg/g[a] ± SE[b] | % FA[c] |
| Eicosatrienoic | C20:3n6 | 0.41 ± 0.06[e] | 0.17[d] | 0.31 ± 0.06[d] | 0.22[e] | 0.85 ± 0.03[f] | 0.28[f] |
| Arachidonic | C20:4n6 | 2.05 ± 0.07[d] | 0.85[d] | 2.24 ± 0.20[d] | 1.57[e] | 2.74 ± 0.09[e] | 0.89[d] |
| Eicosapentaenoic | C20:5n3 | 0.40 ± 0.03[d] | 0.17[d] | 0.52 ± 0.03[e] | 0.37[e] | 0.54 ± 0.03[e] | 0.17[d] |
| Docosatetraenoic | C22:4n6 | 0.18 ± 0.01[d] | 0.07[d] | 0.24 ± 0.01[e] | 0.17[e] | 0.26 ± 0.01[e] | 0.09[d] |
| Docosapentaenoic | C22:5n3 | 0.68 ± 0.03[d] | 0.28[d] | 0.84 ± 0.06[e] | 0.59[e] | 0.93 ± 0.03[f] | 0.30[d] |
| Total | | 240.95 ± 16.67[e] | 100.00[d] | 142.78 ± 4.72[d] | 100.00[d] | 310.00 ± 20.40[f] | 100.00[d] |

[a]mg/g of freeze dried tissue.
[b]SE = Standard error (n = 20).
[c]% FA = % of total fatty acids identified in sample.
[d,e,f]ANOVA analysis was determined as described in Materials and Methods.
Different superscripts indicate significant difference at P < .01 for pairwise comparisons among the methylation methods. Columns containing mg/g were compared among themselves and columns containing % FA were compared among themselves.

TABLE 5

A comparison of fatty acid concentrations obtained from beef longissimus muscle using direct FAME synthesis or the LECO fat extractor

| Condition | Fatty acid (mg/g dry matter) ± SE[a] |
|---|---|
| Freeze dried tissue[b] | 310.25 ± 18.23 |
| Wet tissue[b] | 312.37 ± 27.51 |
| LECO[c] | 336.59 ± 23.36 |

[a]SE = Standard error (n = 12)
[b]Samples were analyzed by direct FAME synthesis.
[c]Lipid content was determined in freeze dried tissue by the LECO TFE2000 Fat Extractor.

TABLE 6

Direct FAME synthesis of samples from wax esters, cholesterol lipid derivatives and alkyl methane sulfates

| Compound | Acid component | Ester observed |
|---|---|---|
| Palmityl stearate | Stearic | Methyl stearate |
| Stearyl linoleate | Linoleic | Methyl linoleate |
| Cholesteryl oleate | Oleic | Methyl oleate |
| Oleyl methane sulfonate | Methane sulfonic | Methyl methane sulfonate |

TABLE 7

FAME synthesis and respective yields by sodium methoxide, boron trifluoride or direct FAME synthesis when employed on a variety of low value oil mixtures, wastes and animal fats.

| | Sodium methoxide | | Direct synthesis | | Boron trifluoride | |
|---|---|---|---|---|---|---|
| | % Theoretical | SD | % Theoretical | SD | % Theoretical | SD |
| Experiment 1 | | | | | | |
| Soy oil | 10.2 | 3.4 | 99.7 | 2.6 | 16.7 | 4.5 |
| Canola oil | 8.2 | 0.4 | 99.2 | 1.7 | 18.5 | 1.4 |
| Corn oil A | 13.1 | 0.1 | 104.4 | 0.4 | 35.6 | 1.2 |
| Yellow grease A | 7.1 | 0.7 | 94.6 | 0.4 | 35.8 | 0.6 |
| Tallow | 12.0 | 1.0 | 98.8 | 8.7 | 34.3 | 0.3 |
| Yellow grease B | 13.4 | 1.5 | 95.3 | 1.6 | 29.9 | 4.0 |
| Top White Tallow | 13.4 | 2.2 | 97.3 | 0.3 | 34.6 | 1.1 |
| Experiment 2 | | | | | | |
| Corn oil B | 97.8 | 0.3 | 99.5 | 1.7 | | |

LITERATURE CITED (AND INCORPORATED BY REFERENCE HEREIN)

Belury, M. A. 2002. Inhibition of carcinogenesis by conjugated linoleic acid: potential mechanisms of action. J. Nutr. 132:2995-2998.

Bolte, M. R., R. W. Hess, W. J. Means, G. E. Moss, and D. C. Rule. 2002. Feeding lambs high-oleate or high-linoleate safflower seeds differentially influences carcass fatty acid composition. J. Anim. Sci. 80:609-616.

Budge, S. M., and S. J. Iverson. 2003. Quantitative analysis of fatty acid precursors in marine samples: direct conversion of wax ester alcohols and dimethylacetals to FAMEs. J. Lipid Res. 44:1802-1807.

Carrapiso, A. I., and C. Garcia. 2000. Development in lipid analysis: some new extraction techniques and in situ trans esterification. Lipids 35:1167-1177.

Christie, W. W. 2003. Lipid Analysis: Isolation, Separation, Identification and Structural Analysis of Lipids, Third edition. The Oily Press, Bridgwater, England.

Cooper, S. L., L. A. Sinclair, R, G. Wilkinson, K. G. Hallett, M. Enser, and J. D. Wood. 2004. Manipulation of the n-3 polysaturated fatty acid content of muscle and adipose tissue in lambs. J. Anim. Sci. 82:1461-1470.

Folch, J., M. Lees, and G. H. Sloane-Stanley. 1956. A simple method for the isolation and purification of total lipids from animal tissue. J. Biol. Chem. 226:497-509.

Kazala, E. C., F. J. Lozeman, P. S. Mir, A. L. Laroche, D. R. C. Bailey, and R. J. Weselake. 1999. Relationship of fatty acid composition to intramuscular fat content in beef from crossbred Wagyu cattle. J. Anim. Sci. 77:1717-1725.

Kramer, J. K. G., V. Fellner, M. E. R. Dugan, F. D. Sauer, M. M. Mossoba, and M. P. Yurawecz. 1997. Evaluating acid and base catalysts in the methylation of milk and rumen fatty acids with special emphasis on conjugated dienes and total trans fatty acids. Lipids 32:1219-1228.

Lewis, T., P. D. Nichols, and T. A. McMeekin. 2000. Evaluation of extraction methods for recovery of fatty acids from lipid-producing microheterotrophs. J. Microb. Methods 43:107-116.

McCance, R. A. 2002. McCance and Widdowson's: The composition of foods. Royal Society of Chemistry, Cambridge, Great Britain.

Mir, P. S., Z. Mir, P. S. Kuber, C. T. Gaskins, E. L. Martin, M. V. Dodson, J. A. Elias Calles, K. A. Johnson, J. R. Busboom, A. J. Wood, G. J. Pittenger, and J. J. Reeves. 2002. Growth, carcass characteristics, muscle conjugated linoleic acid (CLA) content, and response to intravenous glucose challenge in high percentage Wagyu, Wagyu X Limousin, and Limousin steers fed sunflower oil-containing diets. J. Anim. Sci. 80:2996-3004.

Miki, et al., J. Nutr. Sci. Vitaminol, 2004, 50 121-8

Morrison, W. R., and L. M. Smith. 1964. Preparation of fatty acid methyl esters and dimethylacetals from lipids with boron fluoride-methanol. J. Lipid Res. 5:600-608.

Murrieta, C. M., B. W. Hess, and D. C. Rule. 2003. Comparison of acidic and alkaline catalysts for preparation of fatty acid methyl esters from ovine muscle with emphasis on conjugated linoleic acid. Meat Sci. 65:523-529.

Nuernberg, K., G., Nuernberg, K. Ender, S. Lorenz, K. Winkler, R. Rickert, and H. Steinhart. 2002. N-3 fatty acids and conjugated linoleic acids of longissimus muscle in Beef cattle. Eur. J. Lipid Sci. Technol. 104:463-471.

Palmquist, D. L., and T. C. Jenkins. 2003. Challenges with fats and fatty acid methods. J. Anim. Sci. 81:3250-3254.

Park, S. J., C. W. Park, S. J. Kim, J. K. Kim, Y. R. Kim, K. A. Park, J. O. Kim, and Y. L. Ha. 2002. Methylation methods for the quantitative analysis of conjugated linoleic acid (CLA) isomers in various lipid samples. J. Agric. Food Chem. 50:989-996.

Shahin, A. M., M. K. McGuire, K. L. Ritzenthaler, and T. D. Shultz. 2003. Determination of c9,t11-CLA in major human plasma lipid classes using a combination of methylating methodologies. Lipids 38:793-800.

Sukhija, P. S., and D. L. Palmquist. 1988. Rapid method for determination of total fatty acid content and composition of feedstuffs and feces. J. Agric. Food Chem. 36:1202-1206.

Watt, B. K. 1975. Handbook of the nutritional contents of foods for the United States Department of Agriculture, Dover Publications, New York.

The invention claimed is:

1. A method for preparing fatty acid esters from organic matter, comprising:
    obtaining organic matter comprising at least one fat substituent;
    contacting the organic matter in a reaction mixture with a basic solution under conditions suitable to provide for hydrolytic release of monomeric fatty acids from the at least one fat substituent to provide a base-treated reaction mixture; and
    esterifying the monomeric fatty acids of the base-treated reaction mixture by acidification of the reaction mixture and treating in the presence of an organic alcohol in an amount equal to or greater than: about 5%, 10%; 15%; 20%; 25%; or 30% v/v, to provide for an esterification reaction mixture, wherein water is present in the esterification reaction mixture is an amount equal to or greater than about 4% v/v, and wherein fatty acid esters are provided.

2. The method of claim 1, wherein contacting with the basic solution comprises contacting in the presence of at least one of water, and an organic alcohol.

3. The method of claim 1, wherein the organic alcohol is present in the esterification reaction mixture in an amount equal to or greater than about 20% v/v.

4. The method of claim 1, wherein at least 1% v/v water is present during the contacting with the basic solution, and wherein water is present in an amount less than or equal to 35% v/v during esterification.

5. The method of claim 1, wherein, during at least one of contacting with the basic solution and esterifying by treating with acid, water is present in an amount from about 5% to 40% v/v.

6. The method of claim 1, wherein the base comprises a Lewis base or a mineral base, and where the acid comprises an inorganic or an organic acid.

7. The method of claim 6, wherein the mineral base comprises $X(OH)_n$, wherein X comprises Na, K, Mg, or another metal and n is a value from 1-10, and wherein the acid comprises at least one selected from the group consisting of: $H_2SO_4$, HCl, HBr, $HNO_3$, $H_3PO_4$, $H_2CO_3$.

8. The method of claim 1, further comprising, prior to or during contacting with base, pre-treating or treating the organic matter to increase its surface area to volume ratio.

9. The method of claim 1, wherein, prior to esterifying, undigested solid organic matter, or non-fat containing matter, is removed or otherwise sequestered or separated from the base-treated reaction mixture.

10. The method of claim 9, wherein separation of the undigested solid organic matter from the base-treated reaction mixture comprises at least one of centrifugation, settling, filtering, extraction and phase separation.

11. The method of claim 1, wherein, subsequent to esterifying, fatty acid esters are separated from other components of the reaction mixture by means of at least one of centrifugation, settling, extraction, liquid/solid separation methods, filtration, and phase separation.

12. The method of claim 11, wherein the separation comprises at least one of heating the reaction mixture, cooling the reaction mixture, and altering the polarity of the reaction mixture by addition of water, solvents or other polarity altering agents.

13. The method of claim 1, further comprising, prior to esterifying:
    neutralizing the base-treated reaction mixture to provide for neutralized fatty acids;
    removing, sequestering or otherwise separating the neutralized fatty acids from the neutralized reaction mixture; and
    dissolving the separated fatty acids in the esterification reaction mixture.

14. The method of claim 13, wherein, subsequent to esterifying, fatty acid esters are separated from other components of the reaction mixture.

15. The method of claim, 14 wherein separation of fatty acid esters comprises at least one of centrifugation, settling, extraction, liquid/solid separation methods, filtration, and phase separation.

16. The method of claim 15, wherein the separation comprises at least one of heating the reaction mixture, cooling the reaction mixture, and altering the polarity of the reaction mixture by addition of water, solvents or other polarity altering agents.

17. The method of claim 1, wherein the organic matter comprises algae.

18. A method for preparing fatty acid esters from organic matter, comprising:
    obtaining organic matter comprising at least one fat substituent;
    treating the organic matter to increase its surface area to volume ratio;
    contacting the organic matter in a reaction mixture with a basic solution under conditions suitable to provide for hydrolytic release of monomeric fatty acids from the at least one fat substituent to provide a base-treated reaction mixture;
    removing, or otherwise sequestering or separating undigested solid organic matter or non-fat containing matter from the base-treated reaction mixture; and esterifying the monomeric fatty acids of the base-treated reaction mixture by acidification of the reaction mixture and treating in the presence of an organic alcohol in an amount equal to or greater than: about 5%, 10%; 15%; 20%; 25%; or 30% v/v, to provide for an esterification reaction mixture, wherein water is present in the esterification reaction mixture in an amount equal to or greater than about 4% v/v, and wherein esterified fatty acids are provided.

19. The method of claim 18, wherein, subsequent to esterifying, fatty acid esters are separated from other components of the reaction mixture.

20. The method of claim, 19 wherein separation of fatty acid esters comprises at least one of centrifugation, settling, extraction, liquid/solid separation methods, filtration, and phase separation.

21. The method of claim 20, wherein the separation comprises at least one of heating the reaction mixture, cooling the reaction mixture, and altering the polarity of the reaction mixture by addition of water, solvents or other polarity altering agents.

22. The method of claim 18, wherein contacting and esterification are performed within a single vessel.

23. The method of claim 18, wherein the organic matter comprises algae.

24. A method for fat analysis of organic matter, comprising:
obtaining a sample of organic matter comprising at least one fat substituent;
contacting the organic matter in a reaction mixture with a basic solution under conditions suitable to provide for hydrolytic release of monomeric fatty acids from the at least one fat substituent to provide a base-treated reaction mixture;
esterifying the monomeric fatty acids of the base-treated reaction mixture by acidification of the reaction mixture and treating in the presence of an organic alcohol in an amount equal to or greater than: about 5%, 10%; 15%; 20%; 25%; or 30% v/v, to provide for an esterification reaction mixture, wherein water is present in the esterification reaction mixture in an amount equal to or greater than about 4% v/v, and wherein fatty acid esters are provided; and
performing qualitative or quantitative analysis on the fatty acid esters.

25. The method of claim 24, further comprising, prior to or during contacting with base, pre-treating or treating the organic matter to increase its surface area to volume ratio.

26. The method of claim 24, wherein, prior to performing analysis, fatty acid esters are separated from other components of the esterification reaction mixture, and wherein separation of fatty acid esters comprises at least one of centrifugation, settling, extraction, liquid/solid separation methods, filtration, and phase separation.

27. The method of claim 26 wherein contacting the organic matter with a basic solution and esterification are performed within a single vessel.

* * * * *

UNITED STATES PATENT AND TRADEMARK OFFICE
CERTIFICATE OF CORRECTION

PATENT NO.        : 8,642,348 B2                                    Page 1 of 1
APPLICATION NO.   : 12/522701
DATED             : February 4, 2014
INVENTOR(S)       : O'Fallon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 430 days.

Signed and Sealed this
Twenty-ninth Day of September, 2015

Michelle K. Lee
*Director of the United States Patent and Trademark Office*